US009549847B2

(12) United States Patent
Marx

(10) Patent No.: US 9,549,847 B2
(45) Date of Patent: Jan. 24, 2017

(54) BANDOLIER CARTRIDGE STERILE EYEDROP DELIVERY SYSTEM WITH EYELID RETRACTING LEGS AND EYEDROP DELIVERY CONFIRMATION

(71) Applicant: Alvin J. Marx, San Antonio, TX (US)

(72) Inventor: Alvin J. Marx, San Antonio, TX (US)

( * ) Notice: Subject to any disclaimer, the term of this patent is extended or adjusted under 35 U.S.C. 154(b) by 500 days.

(21) Appl. No.: 14/024,527

(22) Filed: Sep. 11, 2013

(65) Prior Publication Data

US 2014/0088524 A1 Mar. 27, 2014

Related U.S. Application Data

(63) Continuation-in-part of application No. PCT/US2011/051826, filed on Sep. 15, 2011, which is a continuation-in-part of application No. PCT/US2011/028235, filed on Mar. 11, 2011, which is a continuation of application No. 12/722,340, filed on Mar. 11, 2010, now Pat. No. 8,734,408.

(60) Provisional application No. 61/732,334, filed on Dec. 1, 2012.

(51) Int. Cl.
*A61F 9/00* (2006.01)
*A61H 35/02* (2006.01)

(52) U.S. Cl.
CPC .................. *A61F 9/0026* (2013.01)

(58) Field of Classification Search
CPC .................................................... A61F 9/0026
USPC ......... 604/294–297, 299–301, 302, 303, 298
See application file for complete search history.

(56) References Cited

U.S. PATENT DOCUMENTS

| | | | |
|---|---|---|---|
| 1,362,682 A | 12/1920 | Dayton | |
| 2,219,604 A | 10/1940 | Trotter | |
| 2,734,665 A | 2/1956 | Flamm | |
| 3,058,466 A * | 10/1962 | Routsong | A61F 9/0026 604/302 |
| 3,261,355 A | 7/1966 | Burbig | |
| 3,486,663 A | 12/1969 | Humphrey | |
| 3,872,866 A | 3/1975 | Lelicoff | |
| 3,934,590 A | 1/1976 | Campagna et al. | |
| 3,964,638 A * | 6/1976 | Dimauro | A61J 7/0472 221/15 |
| 4,085,750 A | 4/1978 | Bosshold | |
| 4,090,642 A * | 5/1978 | Baker | B65D 75/327 206/221 |
| 4,111,200 A | 9/1978 | Sbarra et al. | |
| 4,115,042 A | 9/1978 | Schroeder | |

(Continued)

*Primary Examiner* — Paula L Craig
(74) *Attorney, Agent, or Firm* — Kammer Browning PLLC

(57) ABSTRACT

An eyedrop delivery system for the automated dispensing of eyedrop solution from bottles and ampoules. The system includes a battery and electronic control circuitry. A sprocket drive motor directs the advancement of a loop cartridge band containing eyedrop solution ampoules, moving each one at a time into position for dispensing. A motor rotates a cam to strike a push rod to compress each ampoule. The system includes an eyelid retracting leg assembly. The cartridge automatically advances the next full ampoule into position for dispensing and pushes the ampoule tip aside. The system helps assure that: (1) a known number of drops are dispensed; (2) the dispensed eyedrop(s) fall on the eyeball (by providing eyelid retracting legs to keep the eye open); and (3) the eyedrop(s) landing on the surface of the eye are confirmed using a drop dispensing sensor pair and a surface of the eye sensor pair.

11 Claims, 14 Drawing Sheets

(56) References Cited

U.S. PATENT DOCUMENTS

| | | | |
|---|---|---|---|
| 4,131,115 A | 12/1978 | Peng | |
| 4,321,916 A | 3/1982 | McKee | |
| 4,336,895 A | 6/1982 | Aleff | |
| 4,349,133 A | 9/1982 | Christine | |
| 4,386,608 A | 6/1983 | Ehrlich | |
| 4,515,294 A | 5/1985 | Udall | |
| 4,543,096 A | 9/1985 | Keene | |
| 4,834,727 A | 5/1989 | Cope | |
| 4,927,062 A | 5/1990 | Walsh | |
| 4,973,322 A | 11/1990 | Jewart | |
| 4,981,479 A | 1/1991 | Py | |
| 5,040,706 A | 8/1991 | Davis et al. | |
| 5,064,420 A | 11/1991 | Clarke et al. | |
| 5,102,008 A * | 4/1992 | Kaufman | A61J 7/0481 221/25 |
| 5,171,306 A * | 12/1992 | Vo | A61F 9/0008 604/295 |
| 5,215,231 A | 6/1993 | Paczonay | |
| 5,261,571 A | 11/1993 | Goncalves | |
| 5,370,267 A | 12/1994 | Schroeder | |
| 5,382,243 A | 1/1995 | Mulholland | |
| 5,401,259 A | 3/1995 | Py | |
| 5,433,190 A * | 7/1995 | Sunalp | A61B 17/0231 600/236 |
| 5,516,008 A | 5/1996 | Rabenau et al. | |
| 5,578,020 A | 11/1996 | Mosley | |
| 5,611,464 A | 3/1997 | Tsao et al. | |
| 5,611,788 A * | 3/1997 | Marchment | A61F 9/0008 604/295 |
| 5,795,342 A | 8/1998 | Shapiro et al. | |
| 5,810,794 A * | 9/1998 | Peplinski | A61F 9/0026 604/295 |
| 5,902,292 A | 5/1999 | Feldman | |
| 5,993,428 A | 11/1999 | Hardge | |
| 6,010,488 A | 1/2000 | Deas | |
| 6,041,978 A | 3/2000 | Hagele | |
| 6,090,086 A * | 7/2000 | Bolden | A61F 9/0026 604/295 |
| RE37,047 E | 2/2001 | Py | |
| 6,241,124 B1 | 6/2001 | Hoyt | |
| 6,336,917 B1 * | 1/2002 | Berke | A61B 3/1208 604/294 |
| 6,371,945 B1 | 4/2002 | Sherman | |
| 6,595,970 B1 | 7/2003 | Davidian | |
| 6,610,036 B2 | 8/2003 | Branch et al. | |
| 6,730,066 B1 | 5/2004 | Bennwik et al. | |
| 6,736,802 B1 | 5/2004 | Recanati | |
| 6,814,265 B2 | 11/2004 | Clifford et al. | |
| 6,941,948 B2 * | 9/2005 | Staniforth | A61J 7/0076 128/203.12 |
| 6,962,266 B2 * | 11/2005 | Morgan | B65D 83/0472 221/25 |
| 7,191,916 B2 | 3/2007 | Clifford et al. | |
| 7,235,065 B1 | 6/2007 | Sorensen | |
| 7,296,710 B2 * | 11/2007 | Petschner | A61F 9/0026 222/103 |
| 7,513,396 B2 | 4/2009 | Pardes et al. | |
| 7,621,273 B2 | 11/2009 | Morton et al. | |
| 8,246,589 B2 * | 8/2012 | Marx | A61F 9/0026 604/298 |
| 8,734,408 B2 * | 5/2014 | Marx | A61F 9/0026 604/298 |
| 2002/0161344 A1 * | 10/2002 | Peclat | A61F 9/0008 604/295 |
| 2004/0039355 A1 | 2/2004 | Gonzalez et al. | |
| 2004/0111070 A1 | 6/2004 | Hanley | |
| 2004/0173642 A1 | 9/2004 | Clifford et al. | |
| 2004/0181195 A1 * | 9/2004 | Bennwik | A61M 11/00 604/296 |
| 2004/0220537 A1 * | 11/2004 | Embleton | A61F 9/0008 604/290 |
| 2005/0131358 A1 | 6/2005 | Skolik | |
| 2005/0147546 A1 | 7/2005 | Long | |
| 2005/0261641 A1 | 11/2005 | Warchol et al. | |
| 2006/0069358 A1 * | 3/2006 | Gerondale | A61F 9/0008 604/298 |
| 2006/0079851 A1 | 4/2006 | Guerrieri | |
| 2006/0264855 A1 | 11/2006 | Goldenberg et al. | |
| 2007/0055208 A1 | 3/2007 | Berger et al. | |
| 2007/0095862 A1 | 5/2007 | Swiss et al. | |
| 2008/0233053 A1 * | 9/2008 | Gross | A61K 9/0048 514/1.1 |
| 2009/0236374 A1 | 9/2009 | Pardes et al. | |
| 2009/0247967 A1 * | 10/2009 | Delli Paoli, Jr. | A61M 16/0666 604/300 |
| 2009/0259204 A1 | 10/2009 | Galdeti et al. | |
| 2009/0293870 A1 | 12/2009 | Brunnberg et al. | |
| 2009/0318883 A1 | 12/2009 | Sugahara et al. | |
| 2010/0022971 A1 | 1/2010 | Marx | |
| 2010/0132704 A1 | 6/2010 | Djinovic | B65D 75/5822 128/203.15 |
| 2010/0222752 A1 * | 9/2010 | Collins, Jr. | A61M 11/065 604/296 |
| 2010/0286633 A1 | 11/2010 | Marx | |
| 2010/0331765 A1 * | 12/2010 | Sullivan | A61M 15/008 604/24 |
| 2013/0006202 A1 * | 1/2013 | Marx | A61F 9/0026 604/290 |

\* cited by examiner

BANDOLIER CARTRIDGE STERILE EYEDROP DELIVERY SYSTEM WITH EYELID RETRACTING LEGS AND EYEDROP DELIVERY CONFIRMATION

CROSS REFERENCE TO RELATED APPLICATIONS

This Application claims the benefit under Title 35 United States Code §119(e) of U.S. Provisional Patent Application Ser. No. 61/732,334, filed Dec. 1, 2012, and the benefit under Title 35 United States Code §120, as a Continuation-In-Part of co-pending PCT Patent Application Serial No. PCT/US2011/051826, filed Sep. 15, 2011, designating the United States, which claims the benefit under Title 35 United States Code §120, of PCT Patent Application Serial No. PCT/US2011/028235, filed Mar. 11, 2011, designating the United States, which itself further claims the benefit under Title 35 United States Code §119(a) of U.S. patent Application Ser. No. 12/722,340, filed Mar. 11, 2010, the full disclosures of which are incorporated herein by reference.

BACKGROUND OF THE INVENTION

1. Field of the Invention

The present invention relates generally to the field of eyedrop dispensing devices. The present invention relates more specifically to devices for facilitating the proper positioning of an eyedrop dispensing device and the automated dispensing of a fixed quantity of sterile eyedrop solution. The present invention also relates more specifically to improvements in an eyedrop delivery system including drop delivery confirmation, variable bottle size accommodation, and improved cushioned orbital lobe contact surfaces.

2. Description of the Related Art

Devices for dispensing eyedrop solutions are known. Generally, a bottle of eyedrop solution includes a drop dispenser that is built into the exit orifice of the container. To dispense the solution, the user squeezes the bottle forcing solution out of the exit orifice and into his or her eye. Many users have trouble with dispensing eyedrops from standard dispensing bottles. The user has a tendency to blink when the drop is about to enter the eye, causing the drop to miss the eye and land on a closed lid or to one side of the eye. Therefore, eyedrop solution is frequently wasted due to the user blinking during the attempted application and the user ends up with eyedrop solution streaming down his or her face. Problems also occur when the user dispenses too much eyedrop solution (too many drops) accidentally. The user may also think that they have dispensed a drop of solution properly when they may not have. Normally, the eye will only hold about 0.6 of a drop. Therefore, some of the drop will typically go onto the eyelid. It is extremely difficult for the user to know whether the proper 60% of the drop actually landed in the eye. In addition, the size of a drop for a given solution may vary significantly in size.

Besides improper usage and subsequent inadequate treatment, waste is another consideration with currently available eyedrop administration. While some eyedrop solutions are sufficiently inexpensive that manufacturers can plan on some waste by the user while designing packaging for the product and fixing a selling price, other eyedrop solutions, being much more expensive, can dramatically increase the cost of eye care if sufficient measures are not taken to reduce the waste normally associated with the administration of eyedrop solutions.

There are, in addition, a number of problems associated with maintaining the sterility of solutions that are dispensed from a large container through a dropper tip that may become contaminated by exposure or contact. All multi dose vials sold in the U.S. contain antiseptic compounds to protect the solution against bacterial and viral contamination. Moreover, organic antiseptics do not kill all bacteria or viruses. These antiseptics are often irritating and may be toxic to the sensitive tissues surrounding and within the eye. For these reasons, individual dosages of sterile eyedrop solutions may be preferable to a simple container holding a quantity of eyedrop solution that may be subject to waste and may also be subject to contamination once the eye drop bottle is opened.

A number of efforts have attempted to resolve the contamination problem. Thomas Keen, in his U.S. Pat. No. 4,543,096, discloses a dispenser with an eyelid opening device. The user is required to place a pair of lid spreading legs on the edge of the eyelids dangerously close to the eye and then press a lever arm to keep the eyelids apart. It is nearly impossible to exert enough pressure on the edge of the eyelid to keep the eye open without injuring the eye. Thomas Sherman, in his U.S. Pat. No. 6,371,945, discloses an attachment for a bottle that includes a ring intended to help align the bottle with the eye. However, no attempt is made to hold the eyelids open. Gary Campagna, in his U.S. Pat. No. 3,934,590, shows a tripod like device for aligning the solution bottle over the user's eye. No attempt is made to hold the lid open. James Davidian, in his U.S. Pat. No. 6,595,970, shows a device for dispensing eye drops. He proposes a dispensing arm, one side of which includes an indentation that receives the user's nose, the other side of which accepts a dispensing bottle. The bottle includes a pair of arms which, when squeezed, impinge on the side walls of the bottle forcing solution out of the bottle and into the user's eye. No attempt is made to hold the user's eyelid open. U.S. Pat. No. 7,191,916 issued to Julia Clifford et al. shows a dispenser that attempts to control the amount of drops that exit a solution holding bottle. The bottle has retractable apertures that capture and release a drop of solution. The devices disclosed in U.S. Pat. No. 4,927,062 (Walsh); U.S. Pat. No. 6,041,978 (Hagele); U.S. Pat. No. 6,010,488 (Deas); and U.S. Pat. No. 4,834,727 (Cope) as well as U.S. Pat. No. 5,902,292 (Feldman), all attempt to position an eyedrop bottle in a correct location above a person's eye, but none include a means to help hold the user's eye lids spread apart in an open position. U.S. Pat. No. 4,321,916 (McKee) discloses an eyelid retractor that is used during ocular surgery or the like. It is not designed to be used with the dispensing of eyedrop solution.

None of the above cited devices safely holds the user's eyelids open while dispensing eyedrops from a standard eyedrop bottle. Additionally, none of the above mentioned patents describe a device that allows the user to dispense a portioned amount of eyedrop solution in an automatic and repeatable fashion. None of the above cited inventions dispenses a precise amount of eyedrop solution and simultaneously holds the user's eyelids open while doing so.

There has been little, if any, effort in the prior art to provide an efficient means for dispensing single dosages of sterile eyedrop solution accurately and completely into the user's eye. What systems that have been developed are generally expensive and involve a one-time use, where the complex device must be disposed of after the individual dosage has been dispensed. None of the above references provide an automated mechanism for dispensing a series of individual measured doses of eyedrop solution under sterile or near sterile conditions into the user's eye accurately and completely along with direct confirmation of the appropriate dispensing action.

Various efforts have been made to provide confirmation of eyedrop delivery to the eye. In the simplest form the user holds a bottle over the open eye, squeezes the bottle, and hopes that a drop finds its way onto the eyeball. Recent improvements to eyedrop delivery are provided by the system disclosed by the same Applicant of the present invention in the various Related Applications cross referenced above.

The Automated Incremental Eyedrop Delivery System with Eyelid Retracting Legs of the referenced disclosures provide elements to assist with keeping the eye open, electromechanical drive system for automated activation of the delivery system, and are designed to utilize existing eyedrop bottles that may vary slightly in size. The present disclosure also provides a number of improvements that help to assure not only that a single drop or a known number of drops are dispensed from the bottle and that the eye remains open, but also that the eyedrop(s) landing on the eye can be confirmed.

SUMMARY OF THE INVENTION

It is therefore a primary object of the present invention to provide an automated eyedrop delivery system that incorporates eyelid retracting legs and a replaceable bandolier loop cartridge containing individually measured doses of an eyedrop solution. The eyedrop solution is kept sterile until it is ready to be dispensed. It is also an object of the present invention to provide an eyedrop dispensing device with a lid spreading structure with its legs based on the orbit that allows the user to accurately position the dispensing device over the eye and maintain the eyelids open to receive the dispensed eyedrop.

Another object of the present invention is to provide a mechanism that delivers individual measured dosages of an eyedrop solution from a sterile ampoule packet contained on a multi-ampoule packet band within the dispensing device.

Another object of the present invention is to provide an eyedrop dispensing device that automatically detects whether the user has properly positioned the dispensing device over the eye before activating the automatic dispensing system.

It is a further object of the present invention to provide an eyedrop dispensing device that alerts the user to the proper positioning of the device and further facilitates the maintenance of the eyelids in an open condition during the dispensing action.

It is a further object of the present invention to provide an eyedrop dispensing device that utilizes a removable and replaceable cartridge containing a number of individual dosage ampoules of the eyedrop solution.

It is a further object of the present invention to provide an eyedrop dispensing device with a replaceable cartridge containing individually measured dosages of an eyedrop solution that is easy for the user to position within the device and additionally easy for the user to remove and replace the cartridge component after a cartridge has been used entirely.

It is a further object of the present invention to provide an eyedrop dispensing device having visible and audible alerts directed to the user to confirm proper placement, positioning, and battery status of the device, during the operation and use of the device by the user.

It is a further object of the present invention to provide an electromechanical eyedrop delivery system that operates in conjunction with a movable bandolier loop cartridge containing a number of individually packaged and positioned eyedrop solution ampoules so as to automatically advance each ampoule into position for dispensing of the solution as directed by the user, and to direct the dispensing of the eyedrop solution by a separate electromechanical means directing the compressing of the ampoule so as to force the single dose of solution through a nozzle structured to dispense the eyedrop solution into the user's eye.

In fulfillment of the above and further objectives, the present invention provides an automated eyedrop delivery system comprising an enclosure housing electronic and electromechanical components for the automated dispensing of eyedrop solution from a number of individually measured and packaged eyedrop solution ampoules. The dispensing device includes an activation button as well as a number of LED indicators to facilitate the user's recognition of the condition of the device and of the eyedrop dispensing action. The main body of the eyedrop delivery device includes a battery power supply, as well as electronic control circuitry for carrying out the method of eyedrop dispensing. A sprocket drive motor directs the advancement of a loop cartridge comprising an oval band containing a number of eyedrop solution ampoules so as to move each of the ampoules one at a time into position for dispensing. A cam drive motor rotates a cam which strikes a push rod that directs a dispensing hammer onto the flexible wall of the individual ampoule reservoir that is in position for dispensing. The cartridge component containing the bandolier shaped (oval) band retaining the individual ampoule packets is positioned within and covered by a cartridge cover which fits over the delivery device housing and engages the appropriate sprocket drive and cam drive components. The entire device is configured with an eyelid retracting leg assembly that includes two J-shaped flex eyelid retracting legs covered with cushioned skin engaging material. The user holds the eyedrop delivery device in one hand, compressing the eyelid leg assembly together, then places the cushioned skin contacting material on the orbital ridge above and below the user's eye, and then releases the spring loaded eyelid retracting legs to facilitate the maintenance of the eye in an open condition. While holding the device in this manner, the user pushes the activation button with a finger of his free hand. A process that initially detects whether the device is appropriately oriented to ensure that the eyedrop falls into the eye, then automatically advances the bandolier cartridge component to the next full eyedrop ampoule for dispensing. The programmed control electronics direct the rotation of the cam component to move an ampoule dispensing hammer which compresses the ampoule aligned for dispensing and thereby discharging a dose of solution from the device. Various additional condition indicators are provided within the system to facilitate the user's operation of the device and the accurate and complete dispensing of the eyedrop solution into the user's eye.

The present invention also provides an improved eyedrop delivery system that helps to assure that: (1) a single drop or a known number of drops are dispensed from the bottle; (2) the eyedrop(s) fall on the eyeball by providing eyelid retracting legs to keep the eye open; and (3) the eyedrop on the eye can be confirmed using a drop dispensing sensor and a surface of the eye sensor. In addition, it is desirable that any device used to assist in keeping the eye open be cushioned and comfortable to the user. Finally, it would be desirable if an eyedrop delivery system could easily accommodate a variety of different sized eyedrop bottles without losing its single drop sensitivity.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 1:
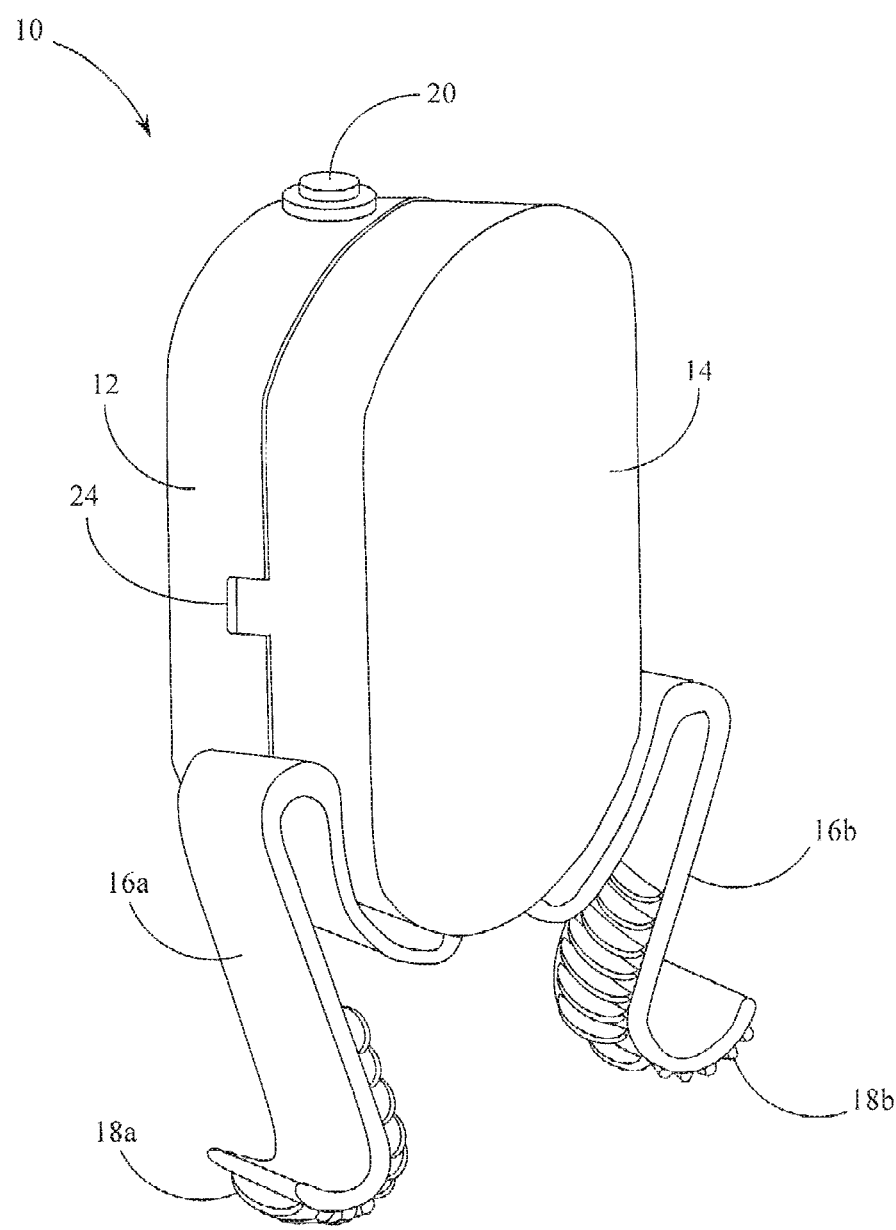
FIG. 1 is a perspective view of a preferred embodiment of the eyedrop delivery system of the present invention shown fully assembled.

Reference is made first to FIG. 1 for a perspective view of a preferred embodiment of the eyedrop delivery system of the present invention in a fully assembled configuration. Eyedrop delivery device 10 is shown to comprise main housing 12 with cartridge cover 14 positioned thereon. The dispensing assembly is positioned on an eyelid retracting assembly made up primarily of first flex leg 16a and second flex leg 16b. Each of the flex legs 16a & 16b extend and terminate in first and second eyelid retracting feet 18a & 18b. This eyelid retracting assembly structure is comprised of a pair of curved bands of resilient, semi-rigid, plastic material that serve to support the housing components described above and to facilitate the retention of the eyelids in an open condition ready to receive the drop of eyedrop solution from an individual ampoule within the device. The eyelid retracting structure accomplishes this by providing flexible, but resilient legs that terminate in soft cushioned feet that are positioned on the upper and lower orbital rim sites of the user's eye.

As shown in FIG. 1, first flex leg 16a and second flex leg 16b extend from near a common point of attachment (away from their point of attachment) to the housing components of eyedrop delivery device 10. Each flex leg 16a & 16b extends downward to terminate in a "J" shaped eyelid retracting foot. First eyelid retracting foot 18a terminates first flex leg 16a, while second eyelid retracting foot 18b terminates second flex leg 16b. As shown, each of the eyelid retracting feet 18a & 18b are covered on at least one face with soft, resilient cushioned material so as to gently engage the skin of the user at the upper and lower orbital sites against which the device and delivery system is placed.

The terms "first" and "second" when referring to the flex legs and eyelid retracting feet, are arbitrary designations herein and do not reflect a specific orientation of the device. The device is designed to be utilized in conjunction with either eye and with either hand of the user. The upper curved sections of flex legs 16a & 16b, on either side of main housing 12, provide the necessary spring resiliency to the eyelid retracting structure so as to allow the user to squeeze the first and second eyelid retracting feet 18a & 18b together for placement of the device against the face about the eye and thereafter release the legs slightly so as to allow for the expansion of the eyelid retracting structure and the corresponding opening of, or retention of the open condition of, the eye of the user.

Various electronic and electro-mechanical components are associated with the operation of eyedrop delivery device 10 as described in more detail below. In the view of FIG. 1, activation button 20 is shown as a surface mounted button positioned on top of main housing 12. Cartridge cover 14 is shown positioned on and attached to main housing 12 by way of cartridge cover clips 24, one on each side of main housing 12.

Figure 2:
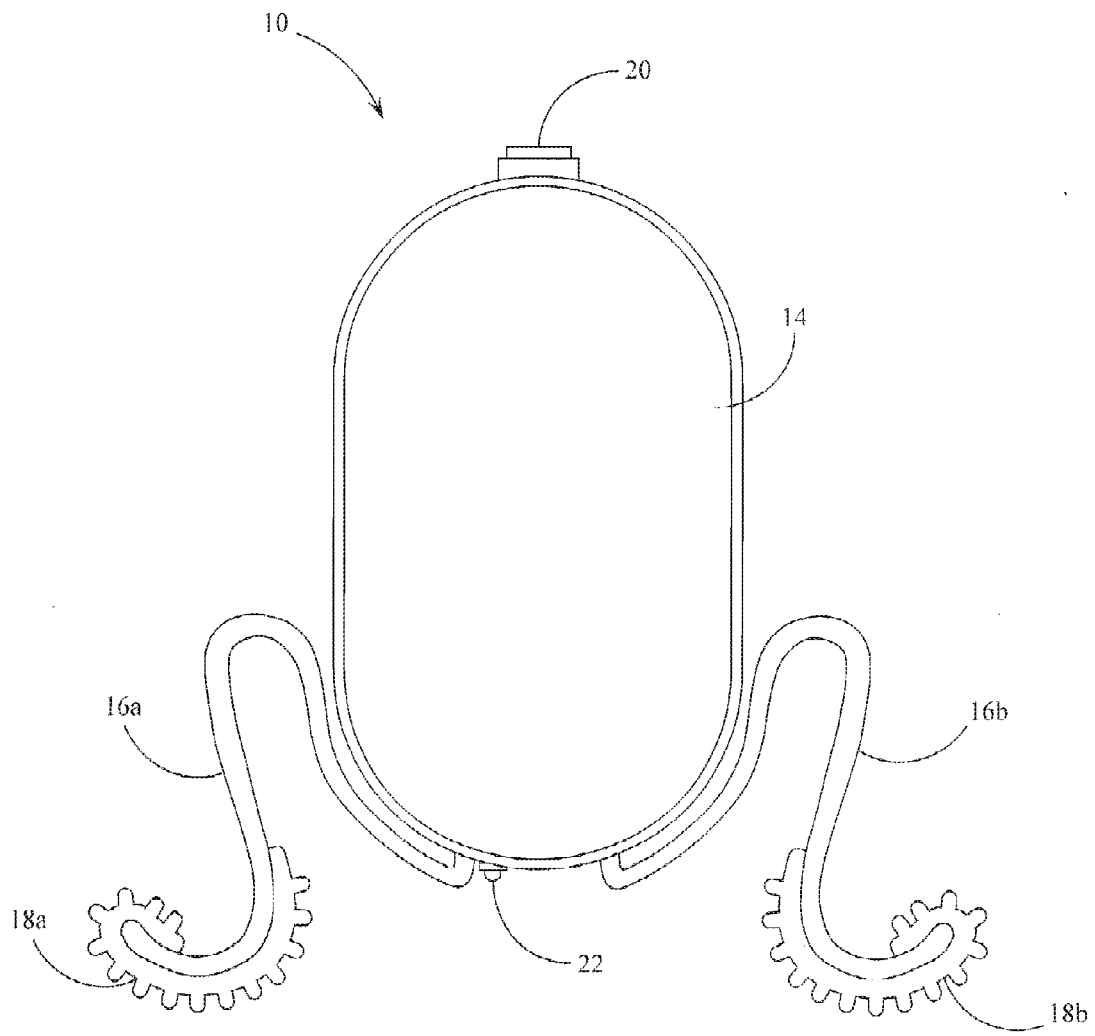
FIG. 2 is a front elevational view of the preferred embodiment of the eyedrop delivery system of the present invention fully assembled.

Reference is next made to FIG. 2 for a detailed description of a front elevational view of the preferred embodiment of the present invention, again shown assembled, with cartridge cover 14 in place over the main housing (not seen in this view). In the view of FIG. 2, the profile structures of the eyelid spreading components (first and second flex legs 16a & 16b, and first and second eyelid retracting feet 18a & 18b) can be seen. The manner in which resiliency is imparted to these components can also be seen, given the curved structures that extend from the base of eyedrop delivery device 10 which are positioned and oriented to facilitate the placement of the device. The legs are first compressed and the feet positioned just inside the upper and lower orbital ridges. The legs are gently released, while the device is kept in place. Activation button 20 is again shown at a top position on eyedrop delivery device 10 accessible for the user to activate the system when delivery device 10 has been properly positioned and oriented over the user's eye. When properly oriented as shown, the user is provided with a view of LED drop indicator 22, as well as an LED battery indicator (not shown), positioned on the bottom of eyedrop delivery device 10. The manner of the function of these LED indicators visible to the user while the device is positioned over the eye is described in more detail below.

Figure 3:
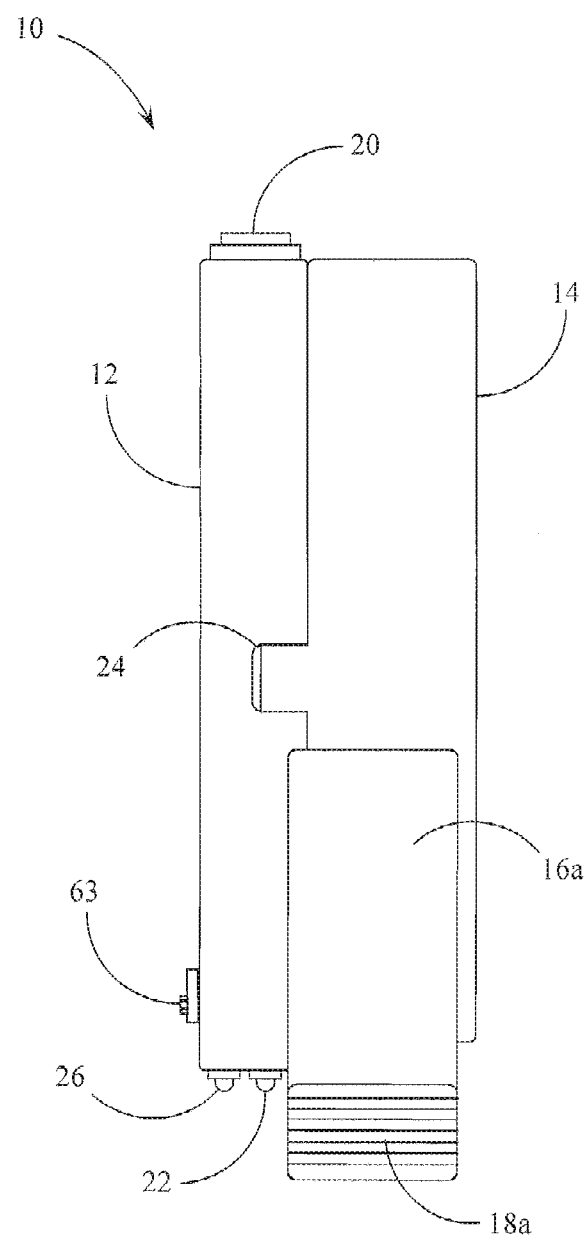
FIG. 3 is a side elevational view of the preferred embodiment of the eyedrop delivery system of the present invention fully assembled.

FIG. 3 is a side elevational view of the preferred embodiment of the eyedrop delivery system of the present invention, again shown in a fully assembled configuration. Eyedrop delivery device 10 is made up primarily of main housing 12 with cartridge cover 14 positioned thereon and attached by means of cartridge cover clips 24. In the view of FIG. 3, only first flex leg 16a and first eyelid retracting foot 18a are visible. Positioned on the bottom of main housing 12 are LED drop indicator 22 and LED battery indicator 26.

As can be seen in the views of FIGS. 1-3, the device of the present invention provides a very simple and straight-forward set of indicators and controls to the user. After the user has properly positioned and placed the device against the face over the eye in the manner described above, both visible and audible indicators provide information regarding the proper orientation and battery condition of the device. Operation of the device is then a simple matter of the user pressing activation button 20 with a finger of the hand that is not holding the eyedrop delivery device 10 against the face. One goal of the present invention is to make the delivery of a single drop (or a fixed incremental quantity) of eyedrop solution to the eye in a definitive manner that leaves no doubt in the user that the drop has been delivered to the proper place on the surface of the eye, thereby eliminating the need for re-administration of an eyedrop that may not have been properly administered.

Figure 4:
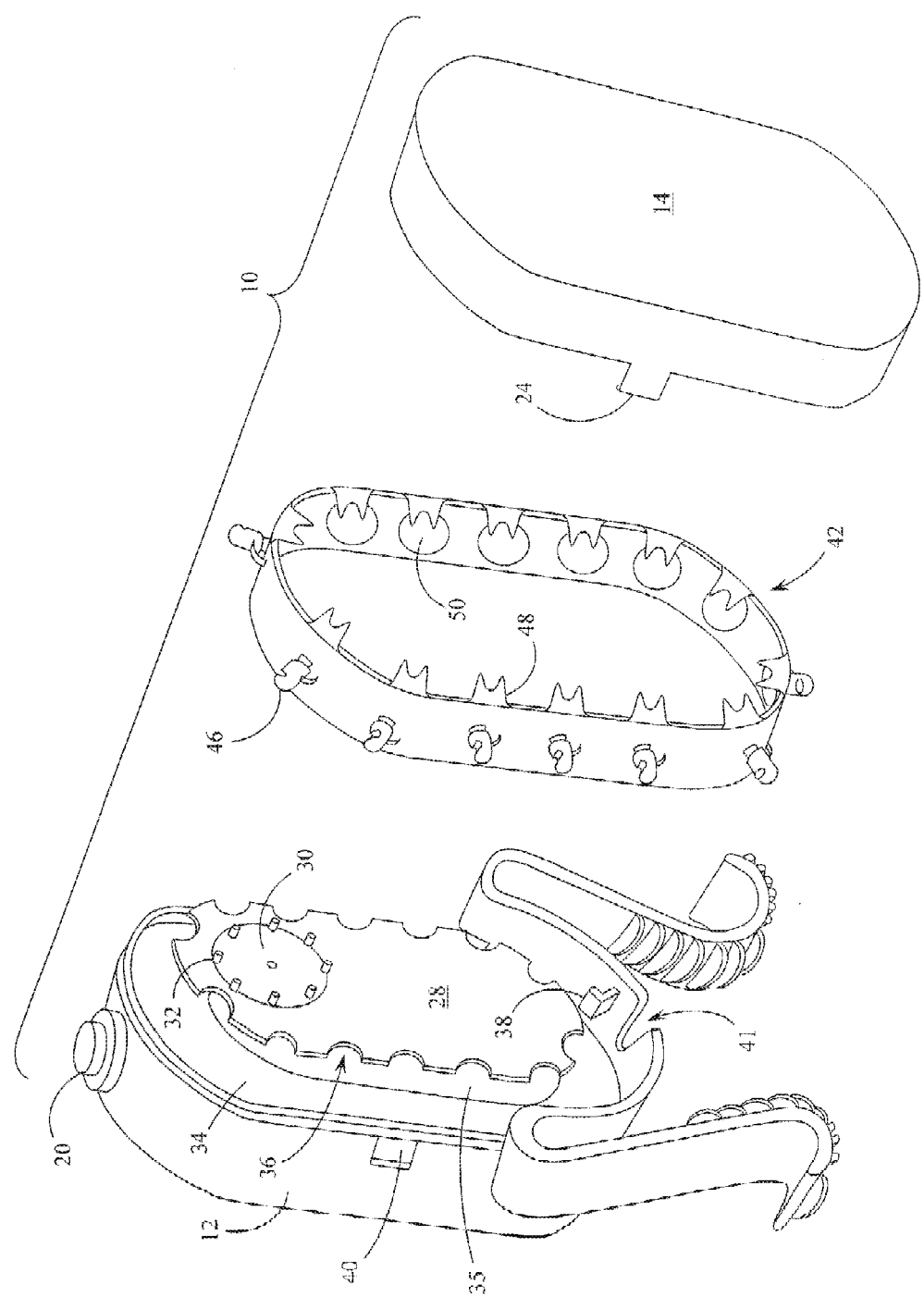
FIG. 4 is an exploded assembly view of the preferred embodiment of the eyedrop delivery system of the present invention.

Reference is next made to FIG. 4, which is an exploded assembly view of eyedrop delivery device 10 showing the manner in which the user may remove cartridge cover 14 and then remove and replace ampoule strip 42. This assembly view of FIG. 4 also discloses some of the mechanical components that serve to advance the individual eyedrop solution dosages contained on ampoule strip 42. The oval or bandolier shaped strip is pre-packaged with individual ampoule reservoirs 50 filled with the appropriate dosage of eyedrop solution. In FIG. 4, main housing 12 of eyedrop delivery device 10 is shown with cartridge cover 14 removed. The eyelid retracting components are again shown to be integrated into the structure of main housing 12 to facilitate the placement and positioning of the device over the user's eye. Dispensing gate 41 represents a cut-out in the curved structure of the eyelid retracting assembly to the user's eye that permits the movement of a dispensed drop from the dispensing assembly to the user's eye in a manner described in more detail below.

Main housing 12 is again shown to comprise activation button 20 positioned at a top oriented external point. With cartridge cover 14 removed, cartridge cover clips 24 are shown to be released from cover clip recesses 40 on either side of main housing 12. Underneath cartridge cover 14 on main housing 12 are a number of components that serve to partially retain and guide ampoule strip 42 during operation of the eyedrop delivery device 10. Mechanism cover 34 serves to isolate the ampoule strip cartridge system from the internal electromechanical workings of the device within main housing 12. Strip guide base 35 supports ampoule strip guide 28 and defines an oval circumference channel within which ampoule strip 42 rotates or moves. The perimeter of ampoule strip guide 28 is formed with strip installation alignment cutouts 36 that correspond to each of the individual ampoules 50 positioned on ampoule strip 42.

Drive sprocket 30 extends through one side of ampoule strip guide 28 and retains a number of sprocket posts 32 which engage ampoule strip sprocket teeth 48 on ampoule strip 42. When ampoule strip 42 is positioned over ampoule strip guide 28 around strip guide base 35 the ampoule strip is free to rotate or move as controlled and driven by drive sprocket 30 in a manner described in more detail below.

Also shown in the view of FIG. 4 are the individual ampoule reservoirs 50 positioned on the inside face of ampoule strip 42, as well as ampoule caps 46 which cover dispensing nozzles (not seen in this view) until a particular ampoule is positioned and ready for dispensing. Tethered ampoule caps 46 are removed from these dispensing nozzles one at a time as the selected ampoule moves into position over dispensing gate 41. The removal of each ampoule cap 46 is carried out one at a time by hook arm 38. The manner of dislodging ampoule cap 46 in order to expose the ampoule dispensing nozzle is described in more detail below.

Figure 5:
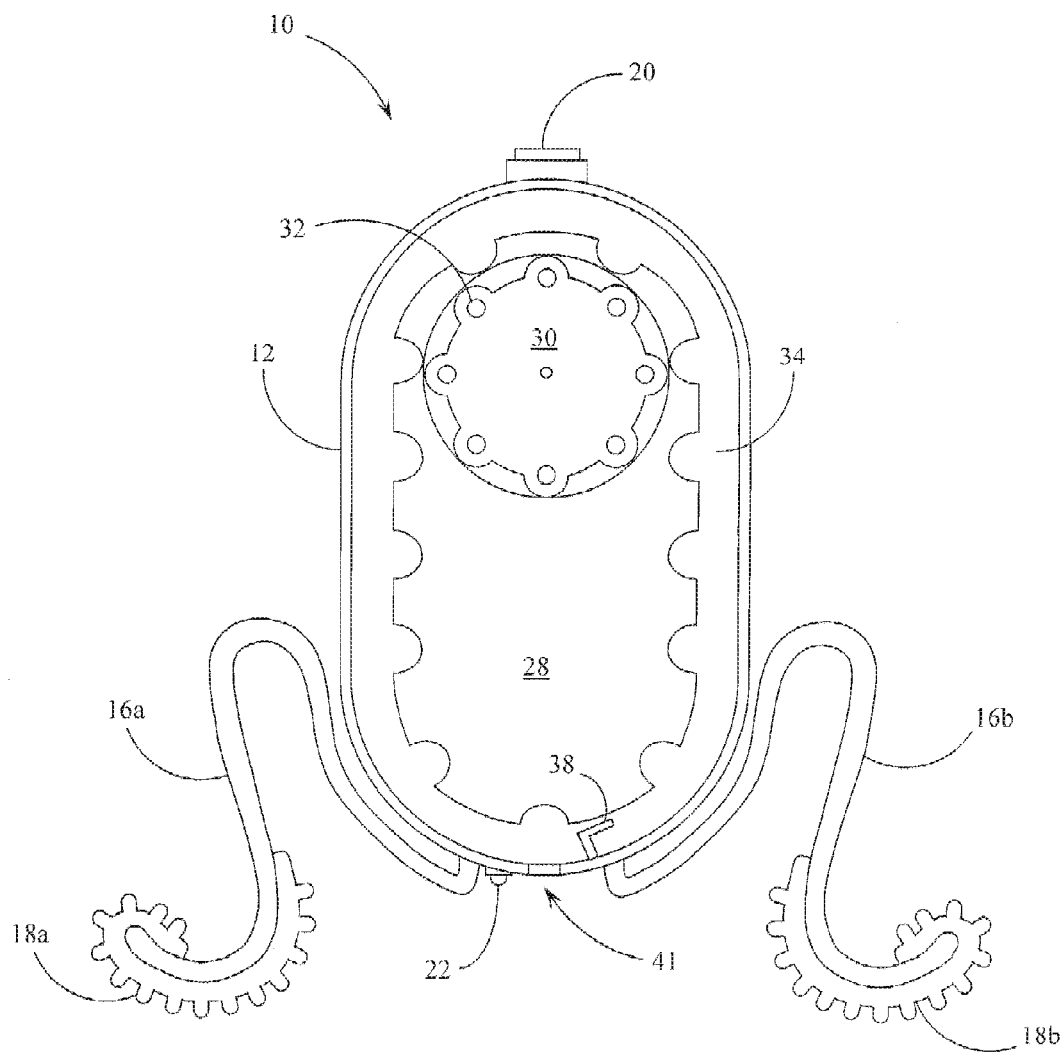
FIG. 5 is a front elevational view of the preferred embodiment of the eyedrop delivery system of the present invention shown without the cartridge cover and ampoule strip in place.

Reference is next made to FIG. 5 which is a front elevational view of the preferred embodiment of the eyedrop delivery system of the present invention shown without the cartridge cover and ampoule strip in place. Eyedrop delivery device 10 in this view is again shown to be structured primarily of main housing 12 integrated with the eyelid retracting structures comprising first and second flex leg 16a & 16b, as well as first and second eyelid retracting feet 18a & 18b. In this view, dispensing gate 41 is shown positioned between the two sides of the eyelid retracting assembly. LED drop indicator 22 is shown positioned adjacent dispensing gate 41 where it is visible to the user while the dispensing device is being used.

Main housing 12 is, in this view, covered by mechanism cover 34 positioned behind ampoule strip guide 28. Drive sprocket 30 extends through ampoule strip guide 28 and presents sprocket posts 32 in a forward orientation so as to engage the ampoule strip sprocket teeth on the ampoule strip (not shown). Hook arm 38 is shown in profile in this view, positioned to appropriately engage the ampoule caps positioned around the perimeter of the ampoule strip.

Figure 6:
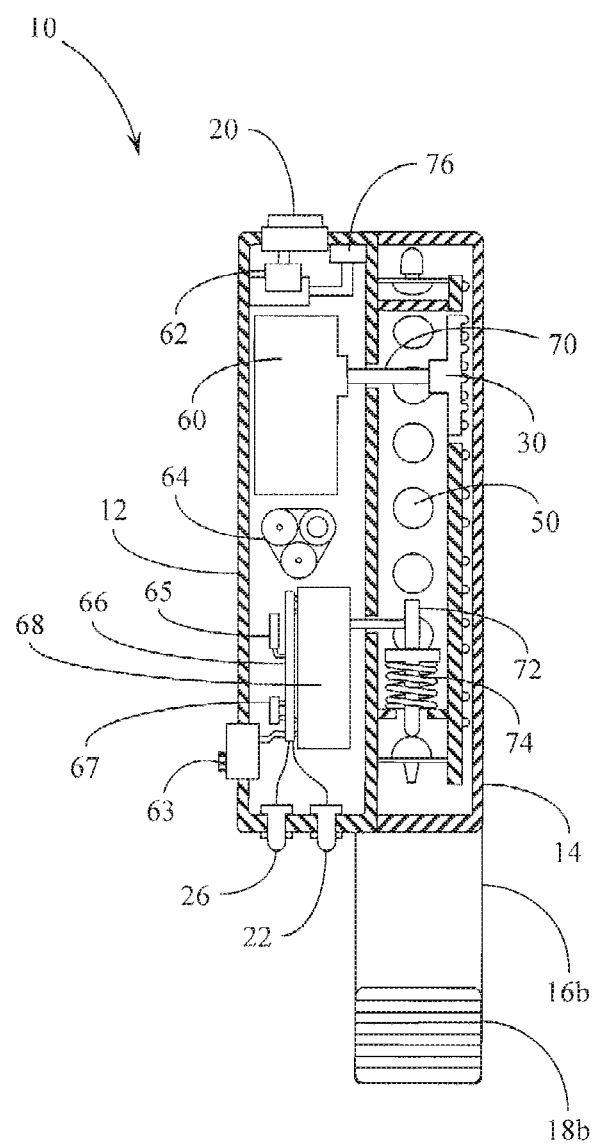
FIG. 6 is a partial cross-sectional side view of the preferred embodiment of the eyedrop delivery system of the present invention showing the internal electronic and electromechanical components.

FIG. 6 provides a partial cross-sectional side view of the preferred embodiment of the eyedrop delivery system of the present invention, disclosing in greater detail both the electro-mechanical components of the device, and the manner in which the dispensing of a single dosage of eyedrop solution is achieved. Eyedrop delivery device 10 as shown in FIG. 6 again comprises main housing 12 fitted with cartridge cover 14. The eyelid retracting components are shown integrated into the lower edge of main housing 12, and in this view are represented by second flex leg 16b and second eyelid retracting foot 18b. Within main housing 12 are positioned and secured a variety of electronic and electromechanical devices that serve to carry out the operation of the system of the present invention. Activation button 20 is shown to extend through the upper wall of main housing 12 where it engages activation switch 62. Switch 62 is preferably a momentary switch that signals the processor circuitry on PC board 66 that the user intends to activate the device. The functionality associated with this initial pressing of activation button 20 and the start of the process for delivering a quantity of eyedrop solution is described in more detail below.

Sprocket drive motor 60 is shown within main housing 12 oriented so as to extend sprocket drive shaft 70 forward to retain drive sprocket 30 which directs and controls the rotation of drive sprocket 30, thereby rotating or advancing the ampoule strip. Also positioned within main housing 12 are batteries 64 which in the preferred embodiment comprise three AAA replaceable batteries. These batteries provide the electrical power necessary to not only run the system electronics, but also to power sprocket drive motor 60 and cam drive motor 68. Cam drive motor 68 is connected by way of a cam shaft to cam 72 seen from the side in this view. Cam 72 rotates on and engages the top of a push rod, which in the view of FIG. 6 is surrounded by push rod spring 74. The bottom or hammer end of the push rod engages the top of one of the ampoule reservoirs 50 positioned on the interior circumferential surface of the ampoule strip.

PC board 66, shown positioned adjacent cam drive motor 68 in the view of FIG. 6, is connected to LED battery indicator 26 and LED drop indicator 22. Microprocessor 67 programmed for carrying out the functionality of the present invention is also positioned on PC board 66 which receives power from batteries 64, directs the necessary signal current to the LED indicators, and the necessary drive current to each of the drive motors contained within main housing 12. When fully assembled in the manner shown in FIG. 6, the system of the present invention advances the ampoule strip incrementally around an oval track, positioning in turn each of the individual ampoules on the ampoule strip at a bottom orientation whereby the rotation of cam 72 and the movement of the push rod downward directs the dispensing of a quantity of eyedrop solution from a single ampoule through the dispensing nozzle for that ampoule and out from the housing.

Figure 7:
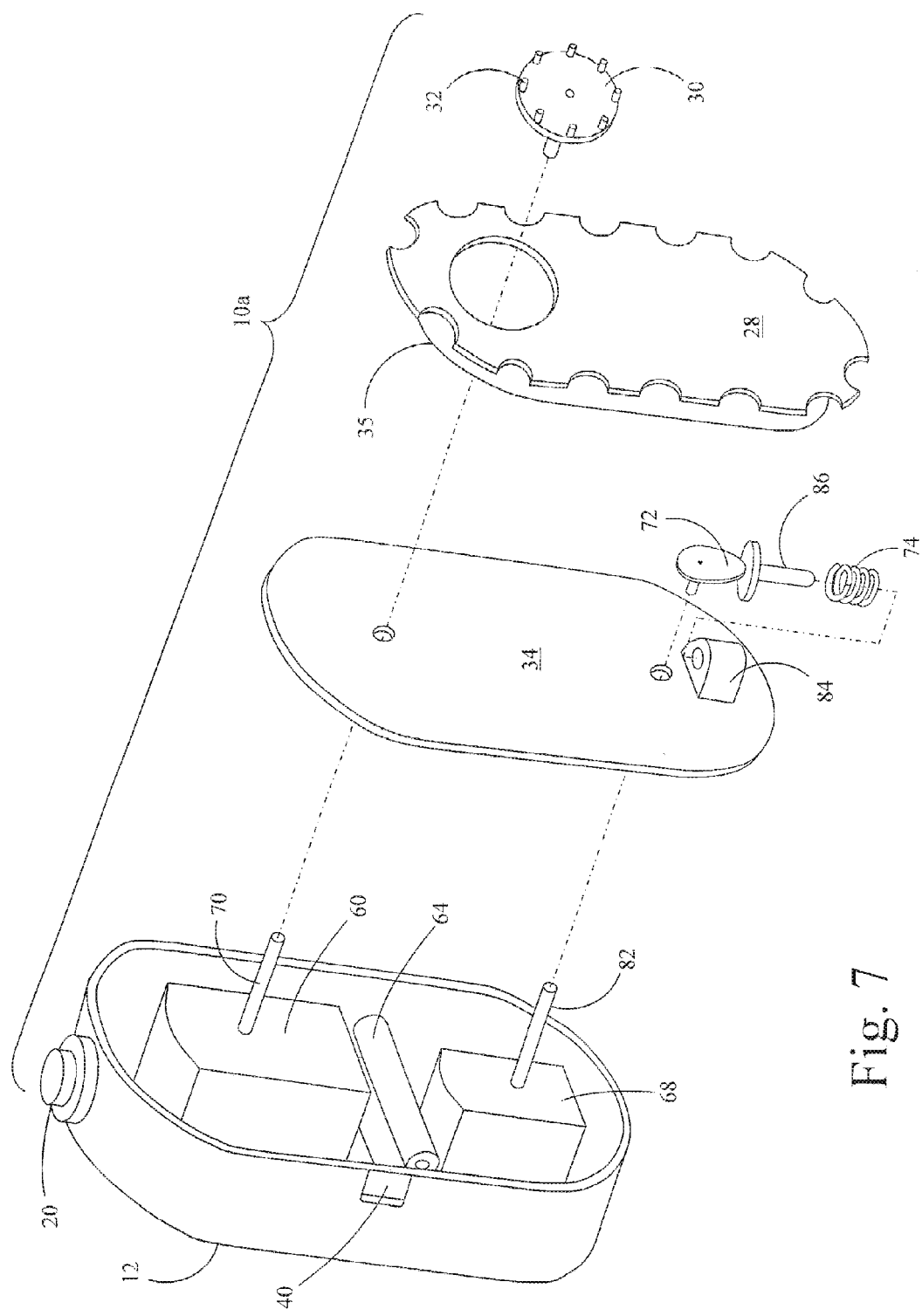
FIG. 7 is an exploded assembly view of a portion of the preferred embodiment of the eyedrop delivery system of the present invention showing the electromechanical components.

Reference is next made to FIG. 7, which provides an assembly view of a sub-assembly of the eyedrop delivery device 10 designated here as 10A, since the ampoule strip and the cartridge cover are not shown in this view. In the view of FIG. 7, main housing 12 is again shown to position activation button 20 at a top orientation thereof, and to have cover clip recesses 40 positioned on either side to receive and retain the cartridge cover (not shown). Positioned within main housing 12 are sprocket drive motor 60 and cam drive motor 68. Sprocket drive shaft 70 extends from sprocket drive motor 60 and cam shaft 82 extends from cam drive motor 68. Batteries 64 are shown positioned between the two drive motors.

Mechanism cover 34 is shown to be an oval plate that may be fixed in position over main housing 12 with a pair of apertures therethrough to allow sprocket drive shaft 70 and cam shaft 82 to operationally extend through mechanism cover 34 to their point of attachment with drive sprocket 30 and cam 72 respectively. Positioned on a lower side of mechanism cover 34 is push rod guide 84 which slidingly retains, and allows the up and down movement of, push rod 86 against the return force of push rod spring 74. When fully assembled, push rod spring 74 holds push rod 86 captive between the top surface of push rod guide 84 and the rotating edge of cam 72. In the view of FIG. 7, the operation of cam 72 can be seen in more detail. The rotation of cam shaft 82 directs the rotation of oblong shaped cam 72 in a manner that allows push rod 86 to raise and lower and thereby direct the hammer end of push rod 86 into the aligned ampoule for dispensing of the eyedrop solution.

Positioned over mechanism cover 34 is ampoule strip guide 28 with strip guide base 35. As can be seen in FIG. 7, one end of ampoule strip guide 28 defines a large round aperture through which drive sprocket 30, having sprocket posts 32, may extend. When drive sprocket 30 is attached to sprocket drive shaft 70, sprocket posts 32 are positioned so as to extend slightly above (forward from) the surface of ampoule strip guide 28. In this manner, the ampoule strip sprocket teeth may slide along the forward facing surface of ampoule strip guide 28 while engaging in turn sprocket posts 32 positioned on rotating drive sprocket 30. This arrangement provides for positive engagement between the ampoule strip and the drive sprocket such that controlled rotation of drive sprocket 30 directs the movement of the ampoule strip in increments to align individual ampoules for dispensing.

Sprocket drive motor 60 and cam drive motor 68, again as shown in FIG. 7 are, in the preferred embodiment, DC stepping motors that allow for precise incremental rotation of their respective drive shafts for precise rotation of either drive sprocket 30 or cam 72. The incremental operation of sprocket drive motor 60 is necessary in order to provide just the right rotation of drive sprocket 30 and therefore just the right rotation and advancement of the ampoule strip so as to sequentially orient and position one ampoule dispensing nozzle after the other in the proper orientation for eyedrop dispensing action. This process of orientation and the manner of moving the ampoule strip into position is described in more detail below. Likewise, cam drive motor 68 is a DC stepping motor that incrementally rotates cam 72 from its two extreme positions; where push rod 86 is fully elevated under the force of push rod spring 74 or fully depressed when cam 72 forces it downward against push rod spring 74. Here again, precise incremental rotation of cam shaft 82 as driven by cam drive motor 68 is essential for the proper operation and full dispensing action of the device.

Figure 8A:
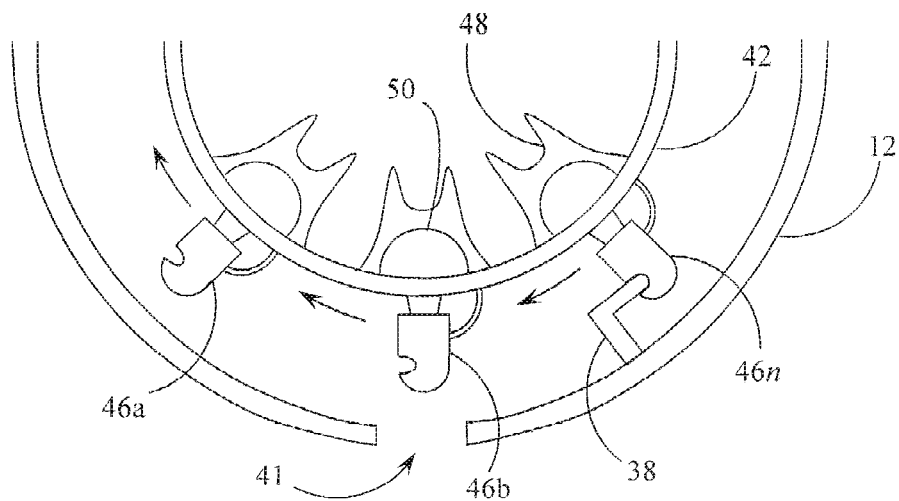
FIG. 8A is a detailed front plan view of the preferred embodiment of the ampoule strip of the present invention shown in an initial position with the caps of the ampoules positioned on the ampoule nozzles.
Figure 8B:
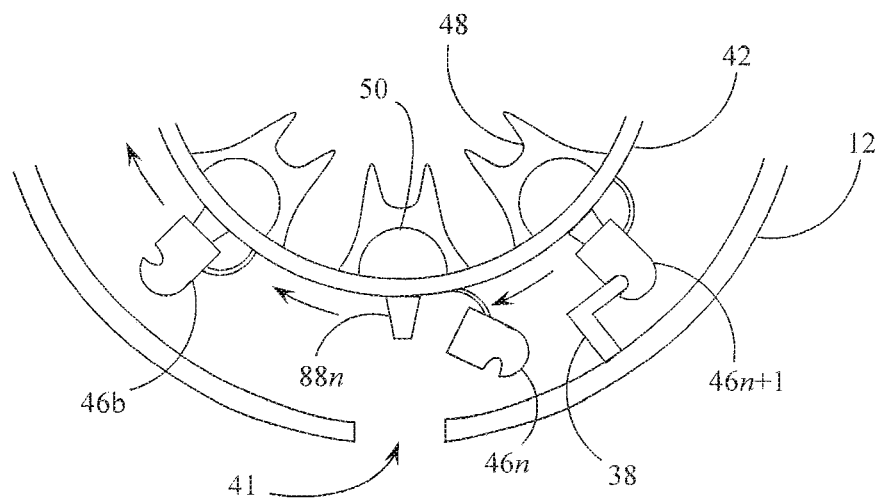
FIG. 8B is a detailed front plan view of the preferred embodiment of the ampoule strip of the present invention shown rotated into a dispensing position with one of the ampoule caps off.

FIGS. 8A & 8B are detailed front views of the dispensing port components of the preferred embodiment of the ampoule strip of the present invention shown first in an initial position with each of the ampoule caps in place (FIG. 8A), each ampoule cap sealed airtight, and second in a dispensing position with one of the ampoule caps removed for dispensing (FIG. 8B). In these figures, a small portion of main housing 12 is shown near the bottom, or dispensing end, of the device. Dispensing gate 41 is oriented so as to allow for the passage of the eye drop solution out from the device into the user's eye in the manner described above. Positioned under the cartridge cover and around the appropriate ampoule strip guide components as described above, ampoule strip 42 advances a number of individual eyedrop solution ampoules one at a time into position for dispensing.

In the views of FIGS. 8A & 8B, three representative ampoules are shown. Ampoule strip 42 is comprised of a flat band through which are positioned a number of ampoule reservoirs 50 and dispensing nozzles 88, as well as corresponding ampoule strip sprocket teeth 48. Once again, the sprocket teeth 48 are provided to engage the sprocket posts of the drive sprocket, not seen in the views of FIGS. 8A & 8B. On the outside of ampoule strip 42 are positioned corresponding dispensing nozzles (covered in the view of FIG. 8A) onto which are positioned a number of ampoule caps 46.

In FIG. 8A, a first ampoule cap 46a is shown positioned as it is initially placed over and retained on the associated dispensing nozzle when the ampoule strip is first inserted into the dispensing device. In the initial condition where eyedrop solution is contained within each of the ampoule reservoirs 50, the ampoule strip 42 is placed within the device and oriented so that ampoule sprocket teeth 48 appropriately engage the posts of the drive sprocket and a single one of the ampoules is oriented in the lowest downward dispensing position. In FIG. 8A, this position is held by second ampoule cap 46b as shown, although the ampoule cap has not been removed (as would be typically when ampoule strip 42 is first installed) and therefore further incremental rotation of the strip is required before dispensing can occur. Hook arm 38 is shown in FIG. 8A to initially engage the N$^{th}$ ampoule cap 46n in a manner that begins the cap removal function. As ampoule strip 42 advances according to the directional arrows shown in FIGS. 8A & 8B, individual ampoule caps 46 are removed to allow the dispensing of the eyedrop solution from the specific ampoule 50.

FIG. 8B shows the next step in the process, where hook arm 38 has dislodged the N$^{th}$ ampoule cap 46n from the dispensing nozzle 88n now in a position to appropriately dispense the eyedrop solution from its ampoule reservoir 50 when the system directs the push rod (not shown) down onto ampoule reservoir 50 in the manner described. Further advancement of ampoule strip 42, as directed by the drive sprocket, positions hook arm 38 appropriately for removal of the next ampoule cap, in this case the N$^{th}$+1 ampoule cap 46n+1. In this manner, the operation of the device progresses, although it is anticipated that the user directs the delivery of one dose eyedrop solution from a single ampoule during each use. Once the device has been activated, and a dose of eyedrop solution has been dispensed, the system remains in the position shown in FIG. 8B until the user next activates the device, which thereafter directs the removal of the next ampoule cap and the rotation of the next dispensing nozzle into position.

Figure 9:
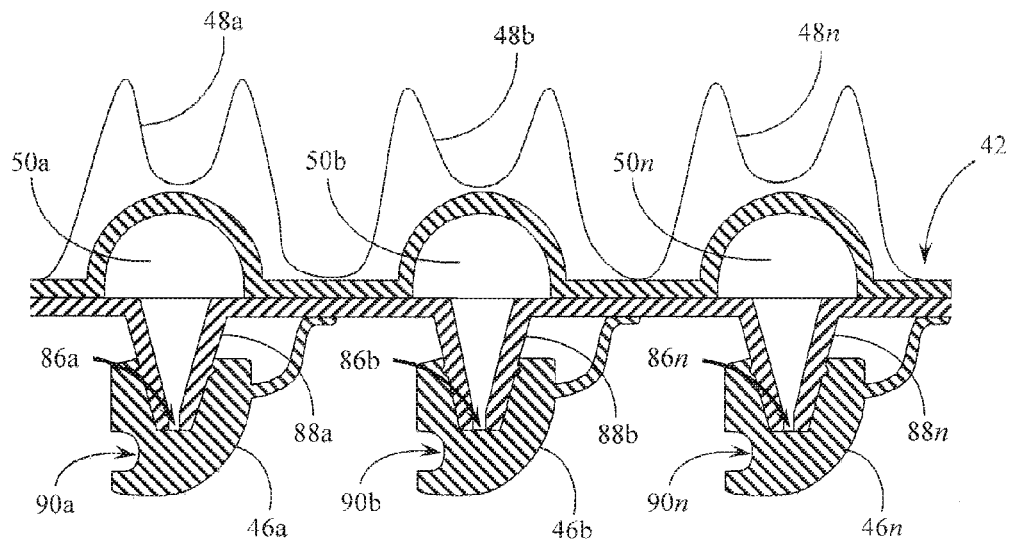
FIG. 9 is a detailed partial cross-sectional view of the preferred embodiment of the ampoule strip of the present invention.
Figure 10:
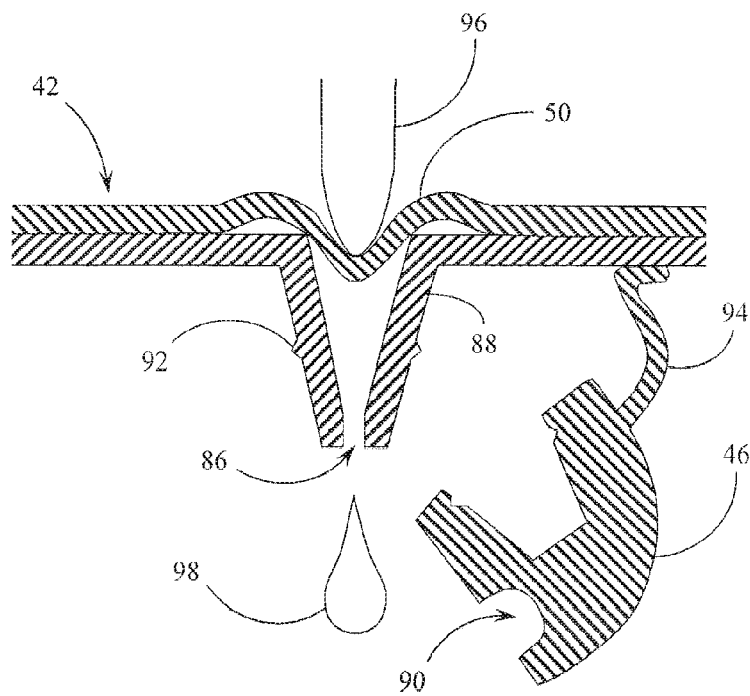
FIG. 10 is a detailed cross-sectional view of the preferred embodiment of a single ampoule of the present invention shown with the cap off and the ampoule wall compressed.

FIGS. 9 & 10 show in greater detail the preferred embodiment of the ampoule strip construction of the present invention. FIGS. 9 & 10 are detailed cross-sectional views of a portion of the ampoule strip showing the construction of the ampoule reservoirs and the ampoule caps that are progressively removed for dispensing. FIG. 9 represents three such ampoule components laid out flat for clarity. First and second ampoule reservoirs 50a & 50b are shown in line followed by a third or N$^{th}$ ampoule reservoir 50n, all positioned on the inside surface of ampoule strip 42. Likewise, first ampoule strip sprocket tooth 48a is followed by second ampoule strip sprocket tooth 48b followed by N$^{th}$ ampoule strip sprocket tooth 48n.

On the outward face of ampoule strip 42 are positioned first, second and N$^{th}$ dispensing nozzles, 88a, 88b & 88n. Each of these dispensing nozzles has a drop aperture represented in this view by first drop aperture 86a, second drop aperture 86b, and N$^{th}$ drop aperture 86n. In the view of FIG. 9, each of the nozzles is covered by its own ampoule cap comprising first ampoule cap 46a, second ampoule cap 46b, and N$^{th}$ ampoule cap 46n. Each ampoule cap is configured with a recess comprising a cap catch represented here by first cap catch 90a, second cap catch 90b, and N$^{th}$ cap catch 90n. The structure of ampoule strip 42 shown in FIG. 9 would be the configuration of the ampoule strip when it is purchased and inserted for the first time into the device of the present invention ready for its first use. This loading of the device may involve the placement of the ampoule strip 42 followed by the placement and positioning of the cartridge cover over the strip. Alternately, the ampoule strip may be loosely held (but accurately positioned) within the cartridge cover so that the loading process may occur in a single step.

FIG. 10 discloses in greater detail the specific action by which a measured dose of an eyedrop solution is dispensed from an individual ampoule. In this detailed cross-sectional view, ampoule reservoir 50 is shown being compressed by dispensing hammer 96 which in the preferred embodiment represents the lower end of the push rod associated with the cam drive mechanism of the device. Dispensing hammer 96 is directed into the bubble shaped wall of ampoule reservoir 50 in a manner that forces the liquid solution from the reservoir through the dispensing nozzle 88 out through drop aperture 86. This arrangement allows the eyedrop solution contained within the ampoule reservoir 50 to be maintained in a generally sterile condition up to the point when ampoule cap 46 is removed as described above. In the detailed view of FIG. 10, ampoule cap 46 is shown to comprise cap catch 90, as well as retainer strap 94 which is attached to the outer surface of ampoule strip 42. Retainer strap 94 is designed to have a shape memory such that once ampoule cap 46 is released from its position over dispensing nozzle 88, it removes ampoule cap 46 sufficiently out of the way to allow dispensing drop 98 to easily fall from drop aperture 86 and out from the device. Ampoule cap 46 is initially retained with an airtight seal on dispensing nozzle 88 against this shape memory of retainer strap 94 by way of retention ridge 92 positioned circumferentially around dispensing nozzle 88 and associated internally to the structure of ampoule cap 46.

Figure 11:
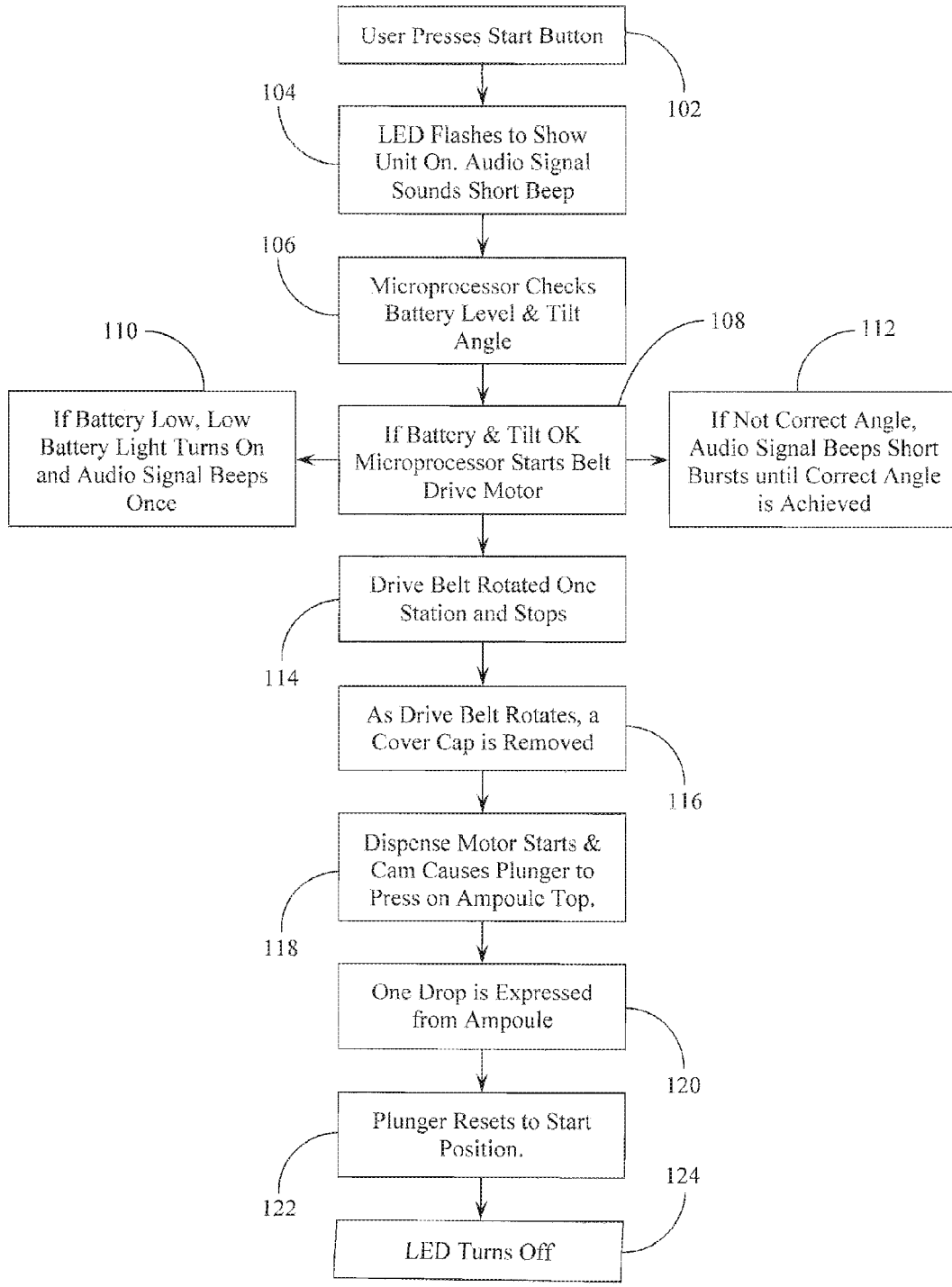
FIG. 11 is a flowchart of the eyedrop dispensing method associated with the system of the present invention.

Reference is finally made to FIG. 11, which provides a brief overview flowchart of the method of operation of the dispensing device system of the present invention. Once the user has appropriately positioned the device against the face, with the legs squeezed and the feet placed just inside the superior and inferior orbital ridges, and has operated the flexible eyelid retracting components, automated operation of the system may begin. This automated operation is initiated at Step 102 when the user presses the start button (the activation button in the structural diagrams described above). At Step 104, a first LED flashes to show that the unit has been turned on. An audio signal sounds a short beep to again confirm activation. At Step 106, the microprocessor determines whether the appropriate battery power level and tilt angle are present.

At decision Step 108, if the battery and tilt angle are appropriate, then the microprocessor starts the drive motor for the ampoule strip. If at Step 112 the correct tilt angle is not present, than an audio signal beeps in short bursts until the correct angle is achieved. This ensures that when a quantity of eyedrop solution is dispensed from an ampoule, it falls by gravity through the opening in the main housing of the device into the user's eye and not to the side.

At Step 110, if the microprocessor determines that battery power is low, the low battery LED turns on (visible to the user) and an audio signal beeps once. In the preferred embodiment of the present invention, the device will not operate beyond the indicator steps when the battery is low. Clearly, proper positioning of the ampoule strip and proper rotation of the dispensing cam are essential to the accurate and complete dispensing of the proper quantity of eyedrop solution from an ampoule.

Once again, at Step 108, if the microprocessor determines that the battery and tilt angle are appropriate, it initiates the drive motor. The drive motor rotates the ampoule strip one increment and stops at Step 114. As the ampoule strip rotates, at Step 116 a cover cap positioned near the base of the device is removed from an individual ampoule as it moves into its dispensing position. Then at Step 118, the dispensing cam motor starts and the cam causes the push rod to impact and press on the top of an individual ampoule. One dosage drop is expressed from that ampoule at Step 120, and because of the appropriate tilt angle, exits the device and is directed properly into the eye of the user. At Step 122, the plunger (push rod) re-sets to its start position (under the force of the return spring) and the device shuts down, this deactivation being indicated at Step 124 when the LED indicator turns off.

Figure 12:
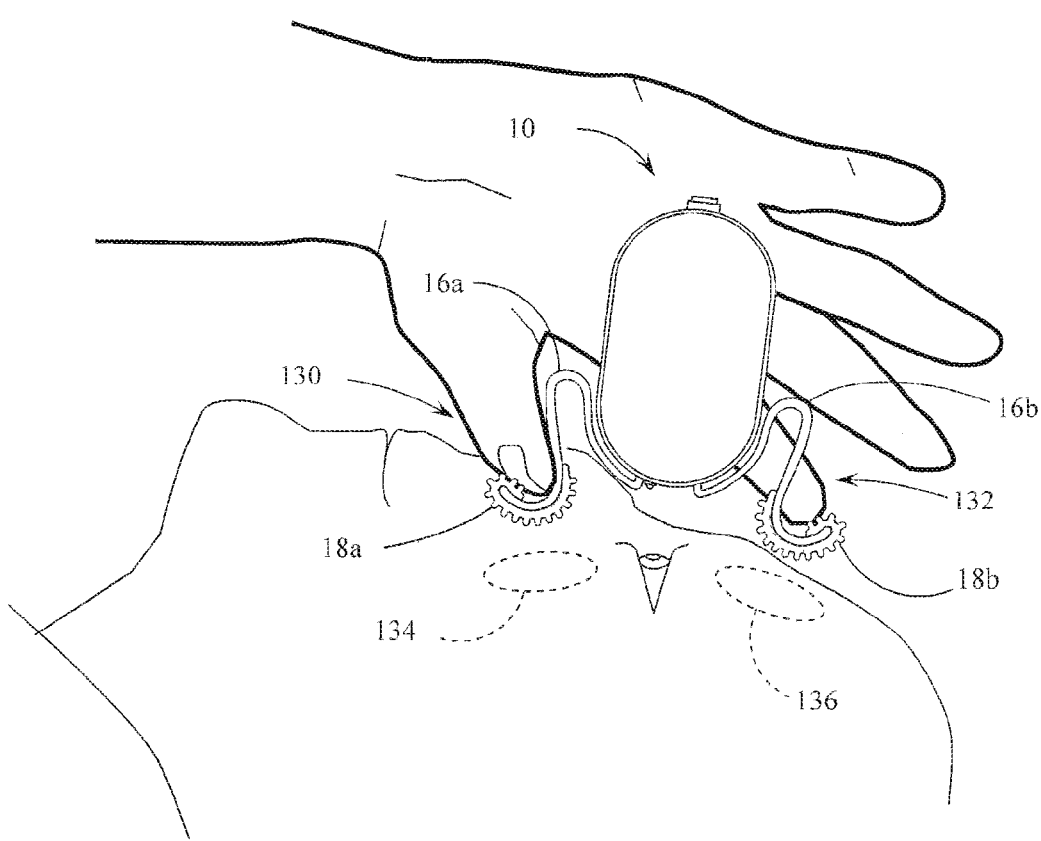
FIG. 12 is a perspective view of a preferred method of use of the device of the present invention.

Reference is now made to FIG. 12 for a description of the manner in which the eyedrop delivery device 10 of the invention is utilized in order to accurately dispense a drop of solution into the user's eye. Oriented in the manner shown in FIG. 12, the user holds the device with the thumb 130 and forefinger 132 engaging first flex leg 16a and second flex leg 16b respectively in a manner that allows the user to initially squeeze the flex legs towards each other and then allow them to return to an extended position once the device has been placed against the skin of the user above the inferior orbital ridge and below the superior orbital ridge of the eye.

Operation of the device of the present invention is facilitated by the user reclining in a horizontal position as shown in FIG. 12 and holding the device in the right hand as shown with the thumb and forefinger engaging the first and second flex legs. As the user holds the device as described above and squeezes the flex legs together, the cushioned surfaces of first eyelid retracting foot 18a and second eyelid retracting foot 18b are placed into contact with the skin of the user just below the superior orbital ridge 136 and just above the inferior orbital ridge 134 of the eyelid portion of the skin surrounding the eye. Once in contact with the skin's surface, the user then gently loosens the compressive force between the thumb and forefinger, all the while keeping the device engaged against the skin. This action of releasing the compressive force allows the eyelid retracting leg assembly to spring back to its original configuration with flex legs 16a and 16b moving outward. As the first and second flex legs move outward, while the eyelid retracting feet remain in gentle contact with the skin of the user about the eye, the eyelids are opened further and/or are retained open by the outward force exerted by the flex legs tending to return to their original configuration. In this manner, the device of the present invention imitates the action of a user that might utilize a thumb and forefinger to hold open the eyelids around the eye while a drop is being dispensed. This use of the present device, however, allows the user a free hand to actually control the dispensing of the eyedrop rather than being required to hold open the eye with one hand in a typically inadequate manner.

The device of the present invention as described above is configured in a sufficiently compact form as to allow the user to push the activation button on the device with the hand that is not holding the device. In any case, once properly positioned and oriented, the user pushes the activation button and causes the device to accurately dispense a single dose of solution into the eye while the eyelids are being retained in an open position by way of the spring force in the flex leg components.

Figure 13:
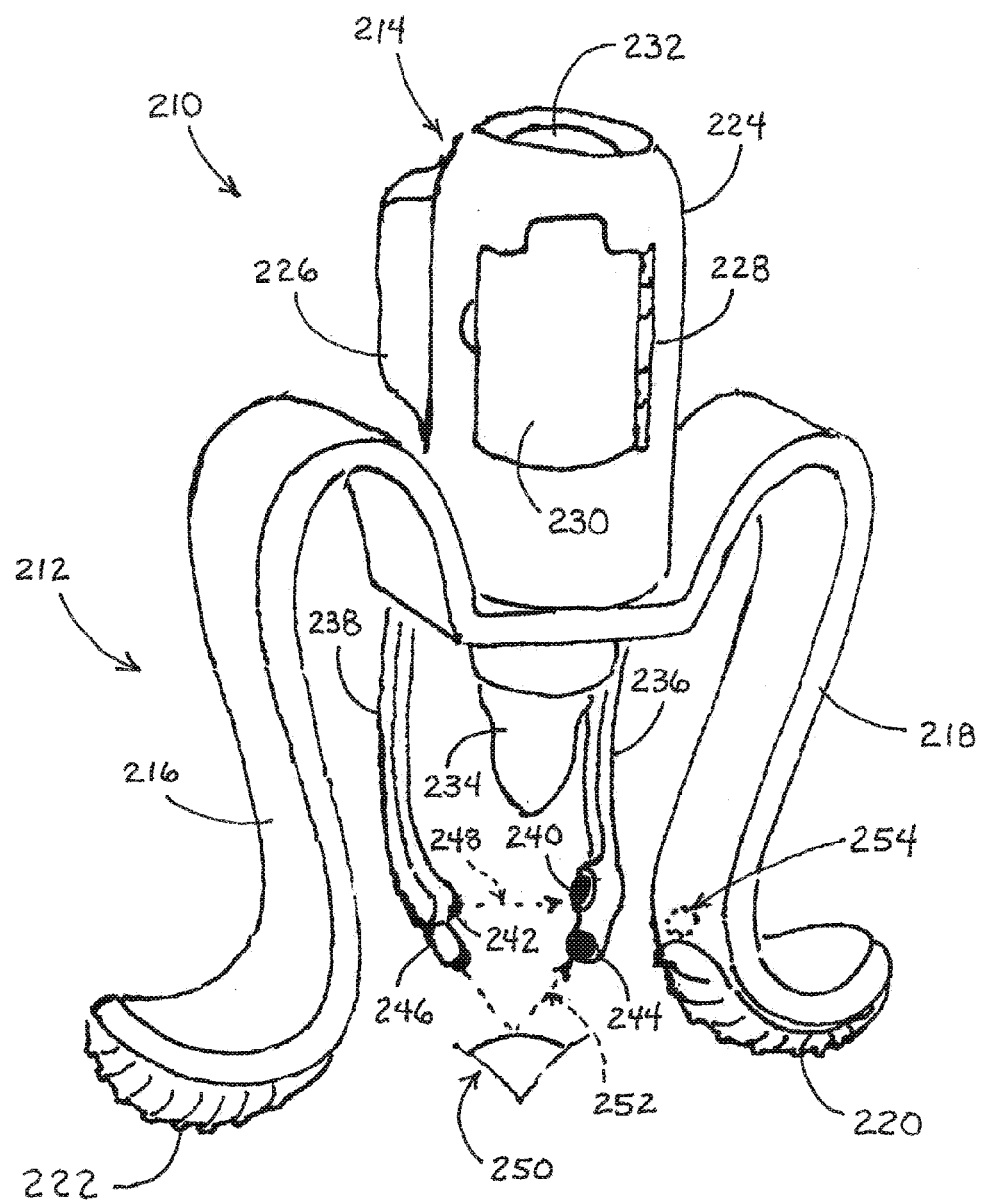
FIG. 13 is a front perspective view of the eyedrop delivery confirmation system of the present invention with the bottle door closed and the device ready for use.

Reference is made next to FIG. 13 which is a perspective view of the device and system of the present invention showing certain further improvements to the Automated Eyedrop Delivery System described in the above cross referenced Related Applications. FIG. 13 shows eyedrop delivery device 210 as being structured to include flexible leg section 212 and eyedrop bottle housing 214. Flexible leg section 212 comprises an eyelid retracting assembly made up of retracting legs 216 & 218. Eyedrop bottle housing 214 is structured and fixed at a mid-point on eyelid retracting assembly of flexible leg section 212 as shown. The dispensing tip of the eyedrop bottle (not shown in FIG. 13) extends through an aperture (also not shown in FIG. 13) in the mid-section of eyelid retracting assembly of flexible leg section 212. Bottle cap 234 is shown positioned over the dispensing tip of the eyedrop bottle as it would be placed when the device 210 is not being used.

Housing 214 is generally made up of an electromechanical system for directing the dispensing of one or more eyedrops from the eyedrop bottle inserted within the housing. As described in the related Application, internal electromechanical components within housing 214 serve to squeeze the inserted eyedrop bottle in an incremental manner so as to dispense one or more eyedrops at a time from the device. Housing 214 generally comprises bottle enclosure 224 and electromechanical enclosure 226. Access to the interior of eyedrop bottle enclosure 224 is provided by way of access door 230 positioned on hinge 228.

The device of the invention as shown in FIG. 13 is activated by pressing on dispense button 232 which directs the electronic circuitry of the device to activate an electric motor (not shown in FIG. 13) and rotate a cam (also not shown in FIG. 13) that impinges upon the side of the eyedrop bottle so as to direct the dispensing of one or more eyedrops.

Also shown in FIG. 13 are sensor arms 236 & 238 that extend down on either side of the tip of the eyedrop bottle (as covered with the bottle cap 234) and terminate in a number of photo-electric sensors that are used to both detect the passage of a drop of liquid between the sensors and to detect the appropriate landing of the eyedrop on the surface of the eye. A first pair of sensors 240 & 242 direct an interruptible beam (such as an IR beam, a visible light beam, or other EM wave beam. The sensor structure is preferably a combination of a photodiode transmitter and receiver that directs a beam across a path 248 interrupted by the drop and detected by the interruption of the signal at the receiver.

A second pair of sensors 244 & 246 are directed downwards at an angle towards the position where the eye of the user would be placed in a manner that bounces a beam (preferably IR or ultrasonic in this case) onto the eye of the user and reflect back (as shown by path 252) to a receiving sensor 244 where the presence of the eyedrop on the eye may be sensed. In each case, it is a change in the sensed signal at the receiving sensors that indicates either the passage of the eyedrop in the first instance or the landing of the eyedrop on the eye in the second instance. Signal interruption or signal strength modification is sufficient in each case to confirm drop passage or drop placement. Alternate to the positioning of the above described sensor structures on special arm extensions as shown in FIG. 13, the sensor elements may be placed within the structure of the flexible leg eyelid spreader leg structures of the eyelid retracting assembly.

The three fundamental improvements made in the device of the present invention to those structures previously described in the related Application (the International Publication mentioned above) are the structure of the eyedrop bottle access door 230 (especially the internal structure described in more detail below), the sensor systems extending below the device towards the eye for both the detecting of the passing of a drop from the dispensing bottle tip and the landing of the drop on the surface of the eye, and finally, the improved composition in structure to the eyelid retracting leg pads 220 & 222 positioned so as to make contact with the orbital lobes of the user in a manner that allows the eyelid to be retracted and the eye to remain open. In the present invention eyelid retracting leg pads 220 & 222 are preferably made from thermoplastic elastomer (TPE) materials such as those produced by GLS (PolyOne Corporation). These materials provide a very soft cushioned contact surface for placement against the very sensitive skin areas around the eye, in particular against the orbital lobe.

Figure 14:
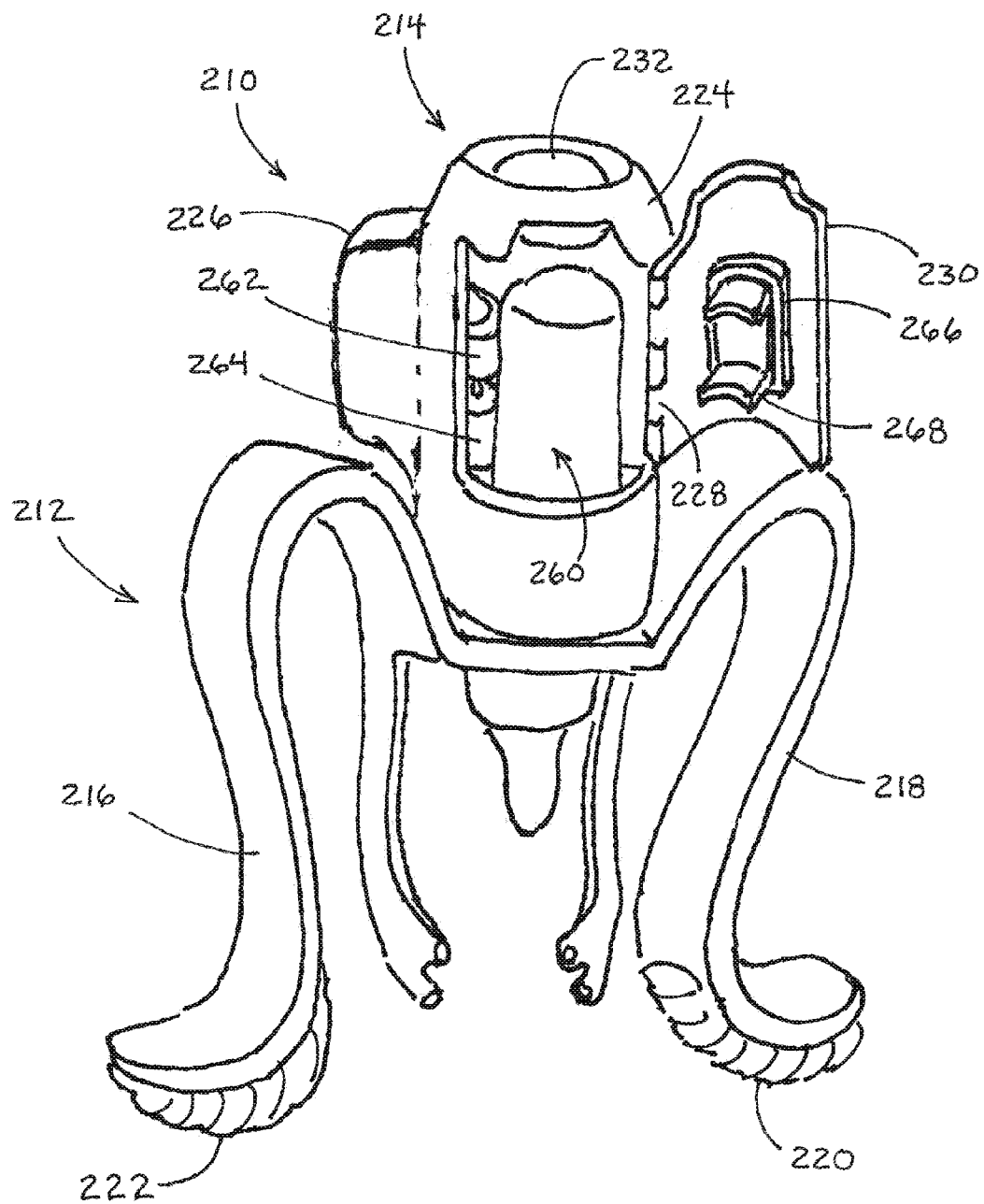
FIG. 14 is a front perspective view of the eyedrop delivery confirmation system of the present invention with the bottle door open showing the inserted bottle and the automated dispensing components.

Reference is next made to FIG. 14 which focuses on the structure of the improvement related to the eyedrop bottle enclosure access door and its internal components designed to accommodate a variety of different eyedrop bottle sizes. In FIG. 14, door 230, which is opened on hinge 228, is shown to include frame 266 positioned on the inside of door 230 and insert 268 positioned on frame 266. As described above, the hinged door can be opened by the user to allow the user to remove and replace the bottle of eyedrop solution. The bottle may come in a variety of different diameters depending upon how many ounces or drops are contained within the bottle. To accommodate the differences in bottle diameter, various sizes of insert 268 fill the distance between the inside of the main housing (as measured from closed door 230) and the side surface of the bottle 260. Insert 268 is snapped into frame 266 which is integral with or mounted to the inside surface of door 230. A variety of different sized inserts 268 are provide in a kit that comes with the device to allow the user to switch out the insert to match the size of the eyedropper bottle being used. In this manner the eyedropper bottle is fit snugly within the enclosure so that activation of the device and the rotation of the cam produces a consistent squeezing of the bottle without any shifting within the enclosure.

Figure 15:
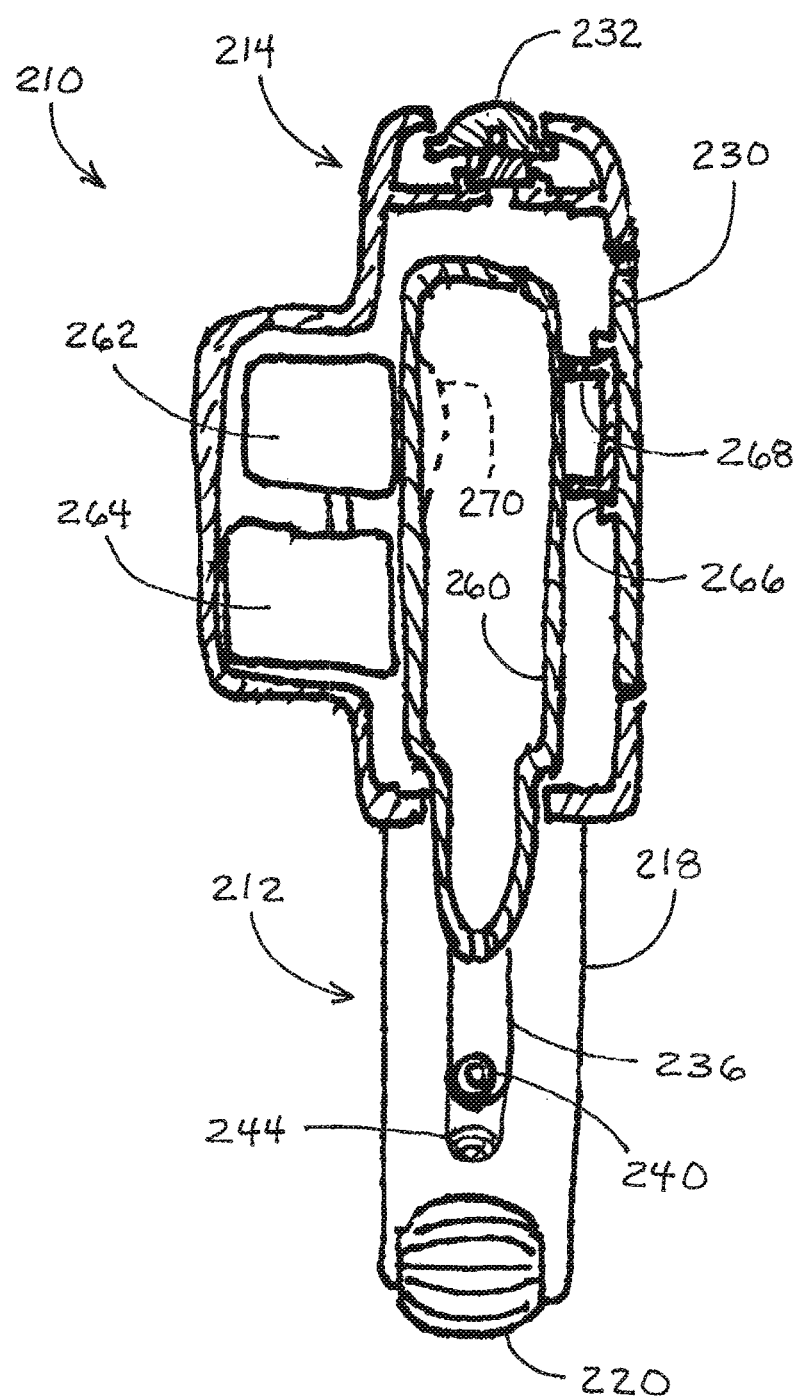
FIG. 15 is a cross-sectional view through the middle of the device of the present invention showing the placement of the bottle, the positioning of the electromechanical components used to squeeze the bottle, and the sensor systems.

Reference is next made to FIG. 15 which is a partial cross-sectional view of the device 210 of the present invention showing not only the placement of eyedrop bottle 260 but also the electromechanical components therein that, once activated, will direct the dispensing of one or more drops from the eyedrop bottle. In this view, insert 268 positioned on frame 266 on the inside of door 230 is shown to contact the side of eyedrop bottle 260 and hold it in place against the pressure exerted by cam 262 driven by electric motor 264. Activation button 232 is shown in its position above the assembly where the user may easily access the button and direct the dispensing of the eyedrop.

The legs of insert 268 are in contact with the outer surface of bottle 260 so that when offset cam 262 driven by motor 264 impinges on the side of bottle 260 as shown by dashed line 270, the insert 268 prevents the bottle from being pushed away from the cam 262. Different inserts 268 having different leg lengths may be snapped into frame 266 depending upon the diameter of the bottle 260 to be used. One half of the sensor pairs are also shown in FIG. 15 with dispense sensor 240 shown above landing sensor 244 (positioned at an angle).

Electronics contained within the electromechanical enclosure 226 provide the necessary circuitry to: (1) receive the signal from the activation button to direct the dispensing of the eyedrop; (2) monitor the drop passage dispensing sensor pair to confirm that a drop has been dispensed (and to count the drops if necessary); and (3) monitor the drop landing sensor pair to confirm that a drop has properly landed on the surface of the eye of the user. Various indicators are anticipated for confirming to the user each of the functions of this system.

Although the present invention has been described in conjunction with certain preferred embodiments, those skilled in the art will recognize that modifications to those embodiments that do not alter the fundamental characteristics of the improvements still fall within the spirit and scope of the spirit of the invention. Although the improvements described in the present application have been shown in connection with a specific automated electromechanical eyedrop dispensing device, those skilled in the art will recognize that these same improvements may be implemented in conjunction with a variety of different eyedrop dispensing devices and are thus not tied directly to the function of the embodiment shown. The sensor systems, for example, may serve to operate in conjunction with an eyedrop dispensing system that incorporates no electromechanical drive elements. These sensor elements could function in association with the appropriate electronic sensor circuitry to respond to the passage of a drop and the landing of the drop on the eye regardless of what motivated the dispensing of the drop from the bottle. In like manner, the improvements to the cushioned feet on the flexible legs of the eyelid retracting assembly of the present invention might be utilized in conjunction with a variety of different eyedrop dispensing devices that incorporate the eyelid retracting assembly.

In contrast, the bottle spacer structures described above associated with the door to the bottle enclosure are specifically related to the function of the device driven by the electromechanical system shown, namely, an electric drive motor connected to a rotating cam. Other variations in the preferred embodiment, such as may relate to size or material composition of the overall enclosure and the eyelid retracting assembly, are anticipated and do not necessarily fall outside the spirit and scope of the present invention.

The invention claimed is:

1. A system for automatically and accurately dispensing measured doses of eye drop solution into the eye of a user, the system comprising:
    (a) a dispenser housing;
    (b) a loop cartridge comprising a plurality of ampoules each containing a dose of eye drop solution, the plurality of ampoules positioned in spaced increments around and through a flexible looped band, the looped band having an interior face and an exterior face, the loop cartridge removably attachable to the dispenser housing, each of the plurality of ampoules positioned in spaced increments around the looped band comprising:
        (i) an eye drop solution reservoir comprising a flexible reservoir wall positioned on the interior face of the looped band;
        (ii) a dispensing port in fluid communication with the eye drop solution reservoir, the dispensing port positioned on the exterior face of the looped band and comprising a nozzle defining a dispensing aperture; and
        (iii) a port cap removably positioned on the dispensing port and sealing closed the dispensing aperture;
    (c) a bi-pedal resilient leg support and positioning structure fixed to and supporting the dispenser housing;
    (d) a movable electromechanical loop cartridge advancement mechanism positioned within the dispenser housing;
    (e) a port cap hook arm fixed within the dispenser housing and oriented to engage and remove the port cap positioned on each dispensing port as the dispensing port is moved into position for dispensing a dose of eye drop solution;
    (f) a movable electromechanical ampoule compression mechanism positioned within the dispenser housing; and
    (g) electronic control circuitry for operational control of the loop cartridge advancement mechanism and the ampoule compression mechanism.

2. The system of claim 1 wherein the bi-pedal resilient leg support and positioning structure comprises:
    (i) a U-shaped frame of semi-rigid plastic material defining a central opening through which a quantity of eye drop solution is dispensed, the U-shaped frame comprising first and second legs extending from a middle portion defining the central opening, the middle portion attached to the dispenser housing;
    (ii) first and second J-shaped feet sections extending from the first and second legs of the U-shaped frame respectively, the J-shaped feet sections extending in a direction back along the legs of the U-shaped frame and spaced therefrom, before curving outward and apart at terminal ends thereof, each leg of the U-shaped frame in combination with one of the J-shaped feet sections, forming a spring compressible by the user to move the terminal ends of the J-shaped feet towards each other, the spring thereafter preferencing the J-shaped feet sections apart; and (iii) cushion pads positioned on the first and second J-shaped feet sections on the outward surfaces of the curved terminal ends thereof;

wherein when the bi-pedal resilient leg support and positioning structure is compressed by the user and the cushion pads engage the orbital ridge of the user, spring preferencing of the J-shaped feet sections facilitates an open condition of the eyelid.

3. The system of claim 1 wherein the looped band of the loop cartridge further comprises a plurality of sprocket teeth positioned on the interior face thereof, and the movable electromechanical loop cartridge advancement mechanism positioned within the dispenser housing comprises:

(i) a stepping drive advancement motor; and (ii) a sprocket drive gear, the sprocket drive gear rotationally driven by the stepping drive advancement motor and engaging the sprocket teeth of the looped band of the loop cartridge;

wherein controlled activation of the stepping drive advancement motor rotates the sprocket drive gear and advances the looped band of the loop cartridge to move one of the plurality of ampoules into position for dispensing.

4. The system of claim 1 wherein the movable electromechanical ampoule compression mechanism positioned within the dispenser housing comprises:

(a) a stepping drive dispensing motor, (b) a rotatable cam, the rotatable cam rotationally driven by the stepping drive dispensing motor;

(c) a dispensing piston comprising a cam surface, a dispensing hammer shaft, and a return spring, the cam surface contacting the rotatable cam and the dispensing hammer shaft contacting one of the plurality of ampoules;

wherein controlled activation of the stepping drive dispensing motor rotates the rotatable cam and directs the movement of the dispensing hammer of the dispensing piston against one of the plurality of ampoules to cause the ampoule to dispense a measured dose of eye drop solution.

5. The system of claim 1 further comprising an activation switch positioned on the dispenser housing and connected to the electronic control circuitry, wherein switching the activation switch directs the controlled motion of the movable electromechanical loop cartridge advancement mechanism and the movable electromechanical ampoule compression mechanism to dispense a dose of eye drop solution.

6. The system of claim 1 further comprising a tilt switch positioned within the dispenser housing and connected to the electronic control circuitry, wherein improper orientation of the tilt switch directs the electronic control circuitry to prevent activation of the movable electromechanical loop cartridge advancement mechanism and the movable electromechanical ampoule compression mechanism and therefore to prevent the dispensing of a dose of eye drop solution.

7. The system of claim 1 further comprising a dispense confirmation indicator positioned on the dispenser housing and connected to the electronic control circuitry, wherein completion of the dispensing of a dose of eye drop solution directs the electronic control circuitry to illuminate the dispense confirmation indicator.

8. The system of claim 7 wherein the dispense confirmation indicator comprises an LED positioned on the dispenser housing at a point visible to the user during the dispensing of a dose of eye drop solution.

9. The system of claim 1 further comprising a battery power supply for providing electrical power to the movable electromechanical loop cartridge advancement mechanism, the movable electromechanical ampoule compression mechanism, and the electronic control circuitry.

10. The system of claim 9 further comprising a low battery indicator and wherein the electronic control circuitry further comprises a low battery condition sensor and an operation interrupt circuit, wherein the operation interrupt circuit prevents the dispensing of a dose of eye drop solution when the battery power supply is below a minimum level.

11. A system for automatically and accurately dispensing measured doses of eye drop solution into the eye of a user, the system comprising:

(a) a dispenser housing;

(b) a loop cartridge comprising a plurality of ampoules each containing a dose of eye drop solution, the plurality of ampoules positioned in spaced increments around and through a flexible looped band, the loop cartridge removably attachable to the dispenser housing;

(c) a bi-pedal resilient leg support and positioning structure fixed to and supporting the dispenser housing, the bi-pedal resilient leg support and positioning structure comprising:

(i) a U-shaped frame of semi-rigid plastic material defining a central opening through which a quantity of eye drop solution is dispensed, the U-shaped frame comprising first and second legs extending from a middle portion defining the central opening, the middle portion attached to the dispenser housing;

(ii) first and second J-shaped feet sections extending from the first and second legs of the U-shaped frame respectively, the J-shaped feet sections extending in a direction back along the legs of the U-shaped frame and spaced therefrom, before curving outward and apart at terminal ends thereof, each leg of the U-shaped frame in combination with one of the J-shaped feet sections, forming a spring compressible by the user to move the terminal ends of the J-shaped feet towards each other, the spring thereafter preferencing the J-shaped feet sections apart; and (iii) cushion pads positioned on the first and second J-shaped feet sections on the outward surfaces of the curved terminal ends thereof;

(d) a movable electromechanical loop cartridge advancement mechanism positioned within the dispenser housing;

(e) a movable electromechanical ampoule compression mechanism positioned within the dispenser housing; and (f) electronic control circuitry for operational control of the loop cartridge advancement mechanism and the ampoule compression mechanism;

wherein when the bi-pedal resilient leg support and positioning structure is compressed by the user and the cushion pads engage the orbital ridge of the user, spring preferencing of the J-shaped feet sections facilitates an open condition of the eyelid.

\* \* \* \* \*